US010457700B2

(12) United States Patent
Dhar et al.

(10) Patent No.: US 10,457,700 B2
(45) Date of Patent: Oct. 29, 2019

(54) PLATINUM PRODRUGS AND METHODS OF MAKING AND USING THEREOF

(71) Applicant: UNIVERSITY OF GEORGIA RESEARCH FOUNDATION, INC., Athens, GA (US)

(72) Inventors: Shanta Dhar, Athens, GA (US); Rakesh Pathak, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 15/555,693

(22) PCT Filed: Mar. 7, 2016

(86) PCT No.: PCT/US2016/021223
§ 371 (c)(1),
(2) Date: Sep. 5, 2017

(87) PCT Pub. No.: WO2016/144889
PCT Pub. Date: Sep. 15, 2016

(65) Prior Publication Data
US 2018/0044362 A1 Feb. 15, 2018

Related U.S. Application Data

(60) Provisional application No. 62/129,364, filed on Mar. 6, 2015.

(51) Int. Cl.
| *A61K 31/282* | (2006.01) |
| *A61K 9/14* | (2006.01) |
| *C07F 15/00* | (2006.01) |
| *A61K 9/51* | (2006.01) |
| *A61K 9/127* | (2006.01) |
| *A61K 31/44* | (2006.01) |

(52) U.S. Cl.
CPC .......... *C07F 15/0093* (2013.01); *A61K 9/127* (2013.01); *A61K 9/14* (2013.01); *A61K 9/51* (2013.01); *A61K 9/5153* (2013.01); *A61K 31/282* (2013.01); *A61K 31/44* (2013.01)

(58) Field of Classification Search
CPC ................ A61K 31/282; A61K 9/14
See application file for complete search history.

(56) References Cited

U.S. PATENT DOCUMENTS

| 4,897,355 A | 1/1990 | Eppstein et al. | |
| 9,556,214 B2 * | 1/2017 | Bilodeau | C07F 15/0093 |
| 2006/0205810 A1 | 9/2006 | Zong et al. | |

FOREIGN PATENT DOCUMENTS

| WO | 2007147373 | 12/2007 |
| WO | 2014100417 | 6/2014 |

OTHER PUBLICATIONS

Hall et al. J. of Structural Biology, 2006, vol. 155, p. 38-44.*
International Search Report and Written Opinion issued in International Application No. PCT/US2016/21223, dated May 12, 2016.
International Preliminary Report on Patentability issued in International Application No. PCT/US2016/21223, dated Sep. 21, 2017.
Barge et al., "Pharmaceutical Salts", J. Pharm. Sci. (1977) 66, 1.
Brigham, et al., "Expression of a prokaryotic gene in cultured lung endothelial cells after lipofection with a plasmid vecto", Am. J. Resp. Cell. Mol. Biol. 1989, 1:95-100.
Brozovic, et al., "The relationship between cisplatin-induced reactive oxygen species, glutathione, and BCL-2 and resistance to cisplatin", Crit. Rev. Toxicol., 2010, 40, 347-359.
Brusamolino, et al., "Efficacy trial of pipobroman in polycythemia vera and incidence of acute leukemia", J. Clin. Oncol. 1984, 2, 558-561.
Dhar, et al., "Current Status and Mechanism of Action of Platinum-Based Anticancer Drugs", Bioinorg. Med. Chem., 2011, pp. 79-95.
Dhar, et al., "Mitaplatin, a potent fusion of cisplatin and the orphan drug dichloroacetate", Proc. Natl. Acad. Sci. USA, 2009, 106, 22199-22204.
Dhar, et al., "Polyvalent Oligonucleotide Gold Nanoparticle Conjugates as Delivery Vehicles for Platinum(IV) Warheads", J. Am. Chem. Soc., 2009, 131, 14652-14653.
Dhar, et al., "Targeted delivery of a cisplatin prodrug for safer and more effective prostate cancer therapy in vivo", Proc. Natl. Acad. Sci. USA, 2011, 108, 1850-1855.
Dhar, et al., "Targeted delivery of cisplatin to prostate cancer cells by aptamer functionalized Pt(IV) prodrug-PLGA—PEG nanoparticles", Proc. Natl. Acad. Sci. USA 2008, 105, 17356-17361.
Felgner et al., "Lipofection: a highly efficient, lipid-mediated DNA-transfection procedure", Proc. Natl. Acad. Sci. USA 1987, 84:7413-7.
Godwin, et al., "High resistance to cisplatin in human ovarian cancer cell lines is associated with marked increase of glutathione synthesis", Proc. Natl. Acad. Sci. USA, 1992, 89, 3070-3074.
Goto, et al., "Overexpression of glutathione S-transferase π enhances the adduct formation of cisplatin with glutathione in human cancer cells", Free Radic. Res., 1999, 31, 549-558.
Graf, et al., "Redox activation of metal-based prodrugs as a strategy for drug delivery", Adv. Drug Deliv. Rev., 2012, 64, 993-1004.
Hamilton, "Picoplatin pharmacokinetics and chemotherapy of non-small cell lung cancer", Expert Opin. Drug Metab. Toxicol. 2013, 9, 1381-1390.
Hamilton, et al., "Augmentation of adriamycin, melphalan, and cisplatin cytotoxicity in drug-resistant and -sensitive human ovarian carcinoma cell lines by buthionine sulfoximine mediated glutathione depletion", Biochem. Pharmacol., 1985, 34, 2583-2586.

(Continued)

*Primary Examiner* — Samira J Jean-Louis
(74) *Attorney, Agent, or Firm* — Meunier Carlin & Curfman LLC

(57) ABSTRACT

Disclosed herein are prodrugs of platinum containing anticancer agents such as cisplatin that contain an alkylating moiety. Upon administration, the prodrugs release the platinum containing anticancer agent and the alkylating agent, which can form an adduct with DNA or can protect the platinum containing agent from removal. The disclosed prodrugs can be used to treat various cancers, including cisplatin resistant cancers.

7 Claims, 14 Drawing Sheets

(56) References Cited

OTHER PUBLICATIONS

Ishikawa, et al., "GS-X pump is functionally overexpressed in cis-diamminedichloroplatinum (II)-resistant human leukemia HL-60 cells and down-regulated by cell differentiation", J. Biol. Chem. 1994, 269, 29085-29093.

Ivanov, et al., "Cisplatin binding sites on human albumin", J. Biol. Chem. 1998, 273, 14721-14730.

Jamieson, et al., "Structure, Recognition, and Processing of Cisplatin—DNA Adducts", Chem. Rev., 1999, 99, 2467-2498.

Jung, et al., "Direct Cellular Responses to Platinum-Induced DNA Damage", Chem. Rev., 2007, 107, 1387-1407.

Kartalou, et al., "Mechanisms of resistance to cisplatin", Mutat. Res., 2001, 478, 23-43.

Kasahara, et al., Metallothionein content correlates with the sensitivity of human small cell lung cancer cell lines to cisplatin,Cancer Res., 1991, 51, 3237-3242.

Kasherman, et al., "Is Glutathione the Major Cellular Target of Cisplatin? A Study of the Interactions of Cisplatin with Cancer Cell Extracts", J. Med. Chem., 2009, 52, 4319-4328.

Kelland, "New platinum antitumor complexes", Crit. Rev. Oncol. Hematol., 1993, 15, 191-219.

Kelland, The resurgence of platinum-based cancer chemotherapy, Nat. Rev. Cancer, 2007, 7, 573-584.

Kelley, et al., "Overexpression of metallothionein confers resistance to anticancer drugs", Science, 1988, 241, 1813-1815.

Kichler, et al., "Efficient gene delivery with neutral complexes of lipospermine and thiol-reactive phospholipids", Biochem. Biophys. Res. Commun. 1995, 209, 444-450.

Kuo, "Redox Regulation of Multidrug Resistance in Cancer Chemotherapy: Molecular Mechanisms and Therapeutic Opportunities",Antioxid. Redox Signal., 2009, 11, 99-133.

Kurokawa, et al., "Effect of Glutathione Depletion on Cisplatin Resistance in Cancer Cells Transfected with the γ-Glutamylcysteine Synthetase Gene", Cancer Science, 1997,88, 108-110.

Mandavilli and M. S. Janes, "Detection of intracellular glutathione using ThiolTracker violet stain and fluorescence microscopy", Curr. Protoc. Cytom., 2010, Chapter 9, Unit 9 35.

Marrache, et al., "Detouring of cisplatin to access mitochondrial genome for overcoming resistance", Proc. Natl. Acad. Sci. USA, 2014, 111, 10444-10449.

Marrache, S. Dhar, "The energy blocker inside the power house: Mitochondria targeted delivery of 3-bromopyruvate", Chem. Sci. 2015, 6, 1832-1845.

Mistry, et al., "Effect of buthionine sulfoximine on PtII and PtIV drug accumulation and the formation of glutathione conjugates in human ovarian-carcinoma cell lines", Int. J. Cancer, 1993, 55, 848-856.

Moller, et al., "Stability, accumulation and cytotoxicity of an albumin-cisplatin adduct", Metallomics 2010, 2, 811-818.

Montero, et al., "Cholesterol and Peroxidized Cardiolipin in Mitochondrial Membrane Properties, Permeabilization and Cell Death", Biochim. Biophys. Acta 2010, 1797, 1217-1224.

Pan, et al., "Reversal of cisplatin resistance in human ovarian cancer cell lines by a c-jun antisense oligodeoxynucleotide (ISIS 10582): evidence for the role of transcription factor overexpression in determining resistant phenotype", Biochem. Pharmacol., 2002, 63, 1699-1707.

Paris, et al., "About the structural role of disulfide bridges in serum albumins: Evidence from protein simulated unfolding" Biopolymers 2012, 97, 889-898.

Pathak, et al., "Copper-Free Click-Chemistry Platform to Functionalize Cisplatin Prodrugs", Chem. Eur. J., 2014, 20, 6861-6865.

Pathak, Set al., "The prodrug platin-A: simultaneous release of cisplatin and aspirin", Angew. Chem. Int. Ed. Engl., 2014, 53, 1963-1967.

Patra, et al., "Hexokinase 2 is required for tumor initiation and maintenance and its systemic deletion is therapeutic in mouse models of cancer", Cancer Cell 2013, 24, 213-228.

Pedersen, "3-Bromopyruvate (3BP) a fast acting, promising, powerful, specific, and effective "small molecule" anti-cancer agent taken from labside to bedside: introduction to a special issue", J. Bioenerg. Biomembr. 2012, 44, 1-6.

Peklak-Scott, et al., "Role of glutathione S-transferase P1-1 in the cellular detoxification of cisplatin", Mol. Cancer Ther., 2008, 7, 3247-3255.

Prescott, Ed., Methods in Cell Biology, vol. XIV, Academic Press, New York, p. 33-71 et seq., 1976.

Rabik, et al., "Molecular mechanisms of resistance and toxicity associated with platinating agents", Cancer Treat. Rev., 2007, 33, 9-23.

Romero-Canelon, et al., "Next-Generation Metal Anticancer Complexes: Multitargeting via Redox Modulation", Inorg. Chem., 2013, 52, 12276-12291.

Russo, et al., "Selective modulation of glutathione levels in human normal versus tumor cells and subsequent differential response to chemotherapy drugs", Cancer Res., 1986, 46, 2845-2848.

Shen, et al., "Cisplatin resistance: a cellular self-defense mechanism resulting from multiple epigenetic and genetic changes", Pharmacol. Rev., 2012, 64, 706-721.

Siddik, "Cisplatin: mode of cytotoxic action and molecular basis of resistance", Oncogene, 2003, 22, 7265-7279.

Suntharalingam, Y. Song, S. J. Lippard, "Conjugation of Vitamin E Analog α-TOS to Pt(IV) Complexes for Dual-Targeting Anticancer Therapy", Chem. Commun. 2014, 50, 2465-2468.

Tew, "TLK-286: a novel glutathione S-transferase-activated prodrug", Expert Opin. Investig. Drugs 2005, 14, 1047-1054.

Torres, et al., "Exploiting cell surface thiols to enhance cellular uptake", Trends Biotechnol. 2012, 30, 185-190.

Wang, et al., "Cellular processing of platinum anticancer drugs", Nat. Rev. Drug Discov., 2005, 4, 307-320.

Wang, et al., "Targeting and delivery of platinum-based anticancer drugs", Chem. Soc. Rev., 2013, 42, 202-224.

Wilson, et al., "Synthetic Methods for the Preparation of Platinum Anticancer Complexes", Chem. Rev., 2014, 114, 4470-4495.

Wisnovsky, et al., "Targeting Mitochondrial DNA with a Platinum-Based Anticancer Agent", Chem. Biol., 20, 1323-1328.

Wong, et al., "Immuno-chemotherapeutic platinum(IV) prodrugs of cisplatin as multimodal anticancer agents", Angew. Chem. Int. Ed. Engl., 2014, 53, 6752-6756.

Zheng, et al., "Pt(IV) Prodrugs Designed to Bind Non-Covalently to Human Serum Albumin for Drug Delivery", J. Am. Chem. Soc. 2014, 136, 8790-8798.

\* cited by examiner

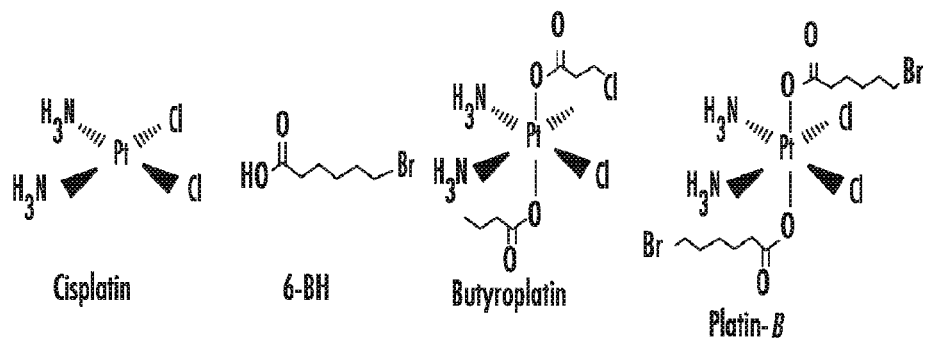
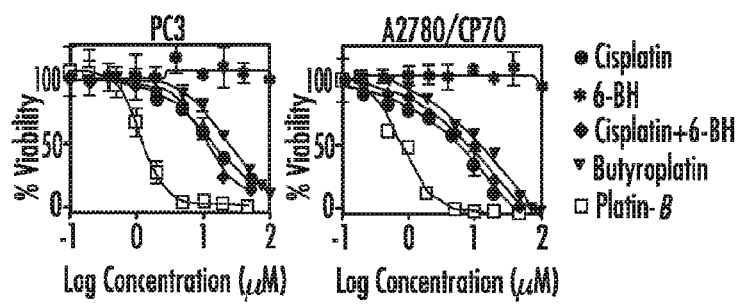
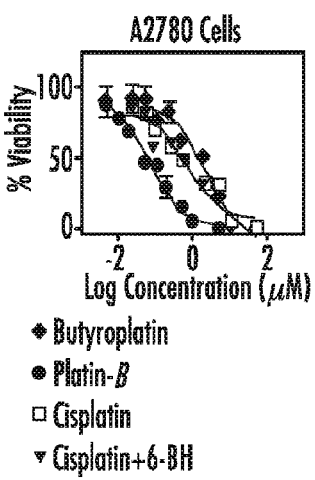
FIG. 4

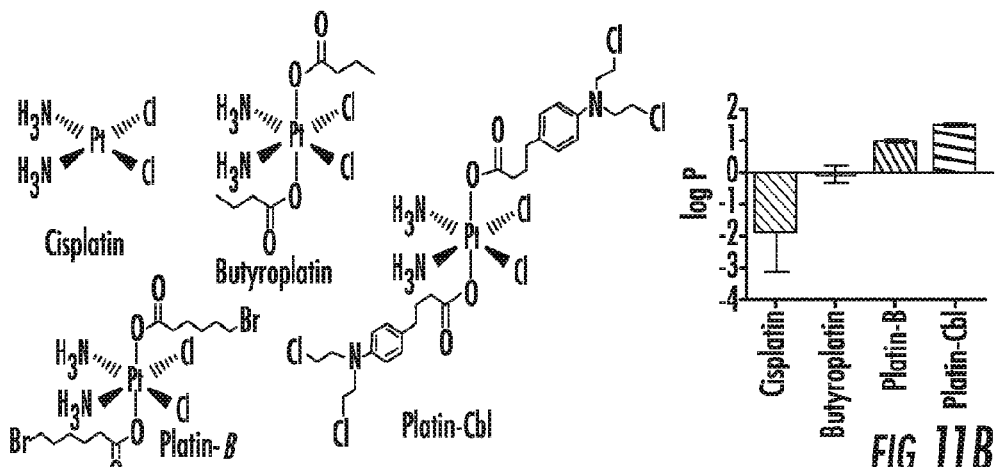
FIG. 11A
FIG. 11B
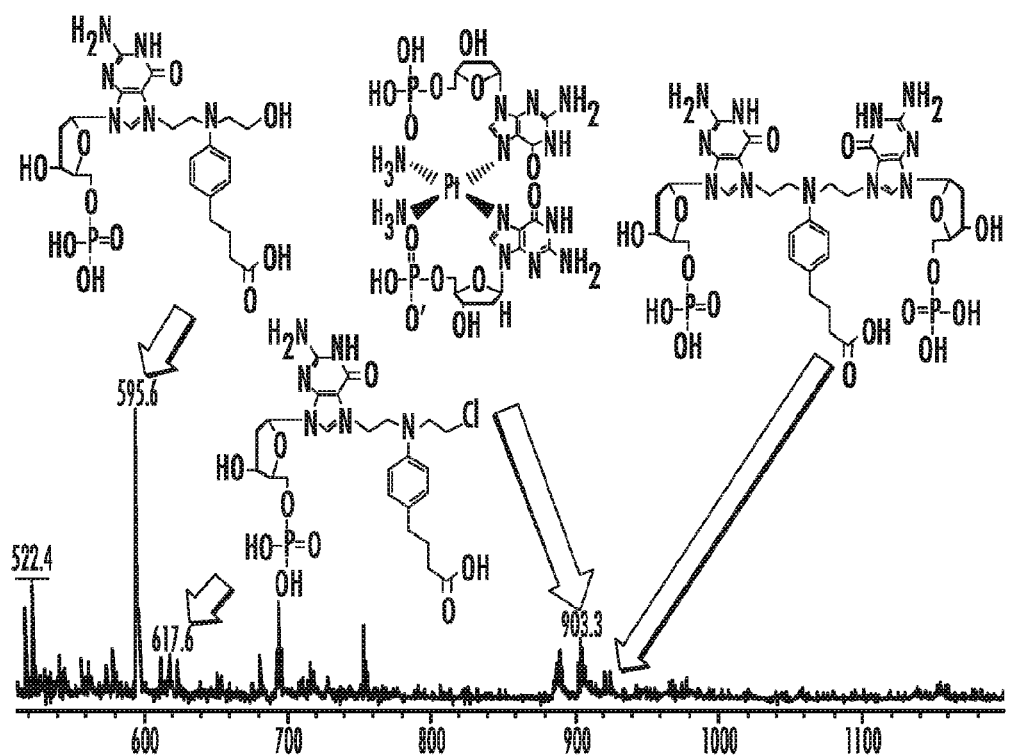
FIG. 11C

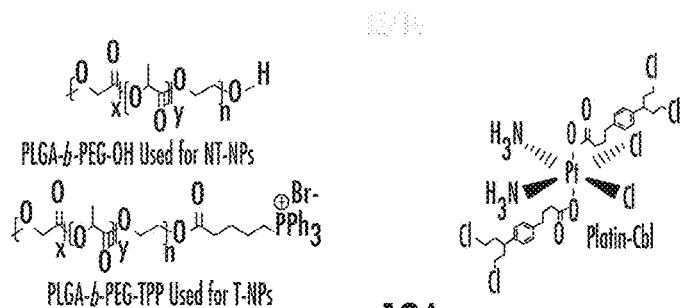
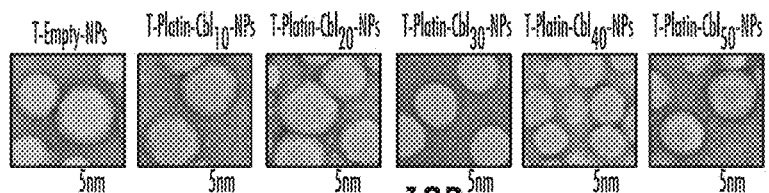
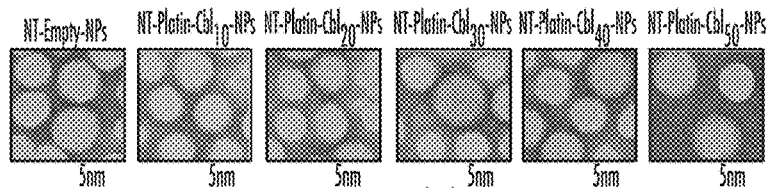
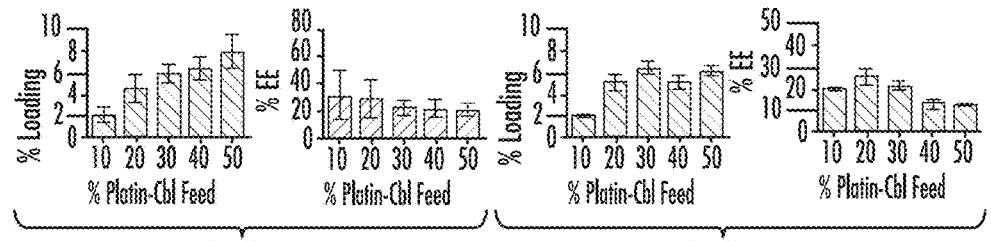
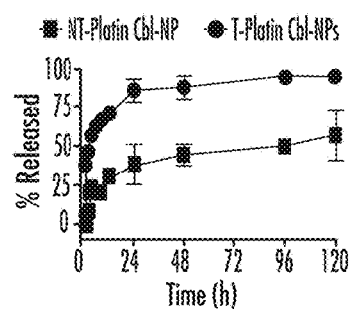

PLATINUM PRODRUGS AND METHODS OF MAKING AND USING THEREOF

CROSS REFERENCE TO RELATED APPLICATIONS

This application claims the benefit of priority to U.S. Provisional Application 62/129,364, filed Mar. 6, 2015, which is hereby incorporated by reference herein in its entirety.

ACKNOWLEDGEMENT OF GOVERNMENT SUPPORT

This invention was made with government support under grant W81XVVH-12-1-0406 awarded by the Department of Defense. The government has certain rights in the invention.

BACKGROUND

Platinum (Pt) compound cis-diamminedichloridoplatinum(II) or cisplatin exhibits clinical activity against solid neoplasms of different kinds (Jamieson et al., Chem. Rev., 1999, 99:2467-2498; Jung et al., Chem. Rev., 2007, 107: 1387-1407; Wang et al., Nat. Rev. Drug Discov., 2005, 4:307-320; Kelland et al., Nat. Rev. Cancer, 2007, 7:573-584; and Dhar et al., Bioinorg. Med. Chem. Wiley-VCH Verlag GmbH & Co. KGaA, 2011, pp 79-95). Initial success of cisplatin treatment regimen to originally sensitive tumor is often associated with chemoresistance (Kartalou et al., Mutat. Res., 2001, 478:23-43; and Siddik, Oncogene, 2003, 22:7265-7279), Colorectal, lung, and prostate cancers are also known to be intrinsically resistant to cisplatin-based therapies (Shen et al., Pharmacol. Rev., 2012, 64:706-721). Major side effects associated with cisplatin therapy are nephrotoxicity, peripheral neurotoxicity, and ototoxicity (Rabik et al., Cancer Treat. Rev., 2007, 33:9-23). However, the main limitation to cisplatin treatment is the high incidence of chemoresistance to escape this cytotoxic compound. Tumor cells develop a myriad of phenotypic changes by establishing a self-defense system, which include decreased cisplatin accumulation with a decline in Pt-DNA adduct, changes in gene expression levels associated with apoptosis, damaged DNA repair, chaperones, transporters, cell cycle arrest, protein trafficking, transcription factors, oncogenes, small GTPases, glutathione (GSH) and its related enzymes, cytoskeletal proteins, and mitochondria.

Further, aquation of cisplatin makes it activated towards the nucleophilic sites on the DNA for its anticancer activity. However, this activated form of cisplatin can also interact with other nucleophilic components, which include GSH and the cysteine-rich metallothionein in the cytoplasm. Thus, increase in such thiols will enhance inactivation and sequestration of cisplatin in the cytoplasm, reduce the availability of the antitumor agent in the nucleus to form DNA adducts, and induce resistance (Godwin, Proc. Natl. Acad. Sci. USA, 1992, 89:3070-3074; Kelland et al., Crit. Rev. Oncol. Rematol., 1993, 15:191-219; Kasherrnan et al. J. Med. Chem., 2009, 52:4319-4328). Studies indicated increased levels of detoxification enzyme (ISH-Stransferase-π, γ-glutamylcysteine synthetase (γ-GCS), and the transcription factor c-Jun in cisplatin resistance tumors (Peklak-Scott et Mol. Cancer Ther., 2008, 7:3247-3255; and Pan et al., Biochem. Pharmacol., 2002, 63:1699-1707). γ-GCS is involved in GSH biosynthesis, ATP-dependent glutathione Sconjugate export (GS-X) pump activity (Kurokawa et al., Cancer Science, 1997, 88:108-110; and Kurokawa et al., Jpn. J Cancer Res., 1997, 88:108-110). An increase in GSH is found in cisplatin resistance and the reaction between actuated cisplatin with GSH can happen either spontaneously or under catalysis by detoxification enzyme GSH-S-transferase-π (Goto et al., Free Radic. Res., 1999, 31:549-558 to form GS-Pt adducts (FIG. 1A). These GS-Pt adducts get excreted out from cells by GS-X export pumps. Additionally, the elevated GSH level contributes to cisplatin resistance due to increased Pt-DNA adducts repair, the capacity to suppress apoptosis by reducing reactive oxygen species (ROS) (Brozovic et al., Crit. Rev. Toxicol., 2010, 40:347-359). Metallothioneins also contribute to cisplatin resistance by deactivating the spontaneously agitated activated cisplatin using the thiol-containing cysteine residues (Kelley et al., Science, 1988, 241:1813-1815; Kasahara et al., Cancer Res., 1991, 51:3237-3242).

What are thus needed are new platinum containing anticancer drugs that can circumvent the resistance and side effects associated with cisplatin treatments. The compositions and methods disclosed herein address these and other needs.

SUMMARY

In accordance with the purposes of the disclosed compounds, compositions, and methods, as embodied and broadly described herein, the disclosed subject matter relates to compositions and methods of making and using the compositions. In further aspects, disclosed herein are compounds having Formula I

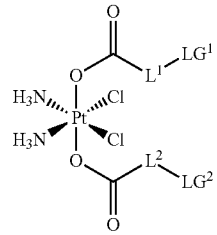

Formula I wherein $L^1$ and $L^2$ are each linker moieties and $LG^1$ and $LG^2$ are each electrophilic leaving groups. These compounds are prodrugs of cisplatin that can be used to overcome chemoresistance and other side effects of cisplatin and other platinum containing anticancer agents. In still further aspects, disclosed herein are compounds of Formulas II to VI, which are prodrugs of other platinum containing anticancer agents. Methods of using the compounds to treat cancers are also disclosed.

Additional advantages of the disclosed subject matter will be set forth in part in the description that follows, and in part will be obvious from the description, or can be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects of the invention and together with the description serve to explain the principles of the invention.

FIG. 4 shows the cytotoxic profiles of Platin-B and comparisons of its $IC_{50}$ values with control compounds shown in the top row in PC3, ovarian cancer A2780, and cisplatin resistant ovarian cancer A2780/CP70 cells. *$P<0.001$; $P=0.001-0.01$; *$P=0.01-0.05$.

FIG. 11, Panel (A), shows structures of different compounds used in the comparison of lipophilicity or log P values. Panel (B) shows a comparison of log P values. Panel (C) shows different adducts formed by Platin-Cbl with guanosine 5'-monophosphate (5'-dGMP).

FIG. 12, Panel (A), shows structures of the polymers and Platin-Cbl used in targeted and non targeted nanoparticles. Panels (B) and (C) show transmission electron micrographs of targeted and non targeted nanoparticles. Panels (D) and (E) show percent Platin-Cbl loading and encapsulation efficiency (EE) Platin-Cbl loaded targeted and non targeted nanoparticles. Panel (F) shows Platin-Cbl release from targeted and non targeted nanoparticles at 37° C.

Figure 1A:
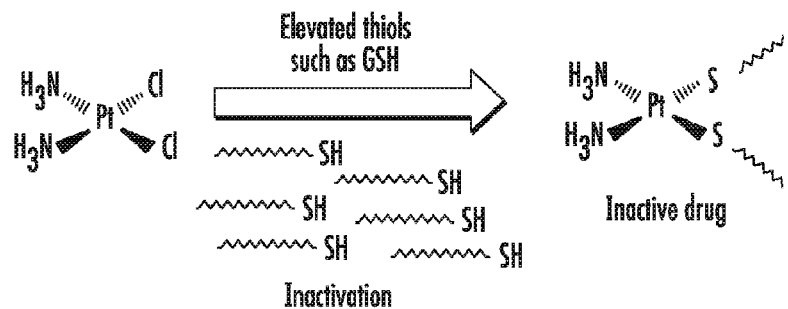
FIG. 1A is a schematic showing the deactivation of cisplatin by cellular thiol containing compounds such as GSH, metallothionein under resistance.

DETAILED DESCRIPTION the compounds, compositions, articles devices, and methods described herein can be understood more readily by reference to the following detailed description of specific aspects of the disclosed subject matter and the Examples and Figures.

Before the present compounds, compositions, and methods are disclosed and described it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Definitions

In this specification and in the claims that follow, reference will be made to a number of terms, which shall be defined to have the following meanings:

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, and the like.

When ranges of values are disclosed, and the notation "from $n_1$ . . . to $n_2$" is used, where $n_1$ and $n_2$ are the numbers, then unless otherwise specified, this notation is intended to include the numbers themselves and the range between them. This range can be integral or continuous between and including the end values. By way of example, the range "from 2 to 6 carbons" is intended to include two, three, four, five, and six carbons, since carbons come in integer units. Compare, by way of example, the range "from 1 to 3 µM,"

which is intended to include 1 µM, 3 µM, and everything in between to any number of significant figures (e.g., 1.255 µM, 2.1 µM, 2.9999 µM, etc.).

The term "about" as used herein is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value itself and the range which would be included by rounding up or down to that figure as well, taking into account significant figures.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, the terms "treating" and "treatment" refer to delaying the onset of, retarding or reversing the progress of, or alleviating or preventing either the disease or condition to which the term applies, or one or more symptoms of such disease or condition.

The term "subject" (and, equivalently, "individual" or "patient") means all mammals including humans. Examples of subjects include humans, cows, dogs, cats, goats, sheep, pigs, and rabbits. Preferably, the subject is a human.

The term "disease" as used herein is intended to be generally synonymous, and is used interchangeably with, the terms "disorder," "syndrome," and "condition" (as in medical condition), in that all reflect an abnormal condition of an individual (e.g., a human or animal body or of one or more of its parts that impairs normal functioning), is typically manifested by distinguishing signs and symptoms, and/or causes the individual to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

The term "therapeutically acceptable" refers to those compounds (or salts, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, amino, carboxylic acid, ester, ether, halide, hydroxy, ketone, or nitro, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, amino, carboxylic acid, ester, ether, halide, hydroxy, ketone, or nitro, as described herein.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, amino, carboxylic acid, ester, ether, halide, hydroxy, ketone, or nitro, as described herein.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, amino, carboxylic acid, ester, ether, halide, hydroxy, ketone, or nitro as described herein.

The term "cycloalkyl" as used herein is a non-aromatic carbon-based ring composed of at least three carbon atoms. Examples of cycloalkyl groups include, but are not limited to, cyclopropyl, cyclobutyl; cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, amino, carboxylic acid, ester, ether, halide, hydroxy, ketone, or nitro.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, amino, carboxylic acid, ester, ether, halide, hydroxy, ketone, or nitro, as described herein.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. Throughout this specification "C(O)" or "CO" is a short hand notation for C=O. A "carboxylate" or "carboxyl" group as used herein is represented by the formula —$C(O)O^-$.

The term "ester" as used herein is represented by the formula —$OC(O)Z^1$ or —$C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are)

selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures. The examples below are intended to further illustrate certain aspects of the methods and compounds described herein, and are not intended to limit the scope of the claims.

Compounds

Figure 1B:
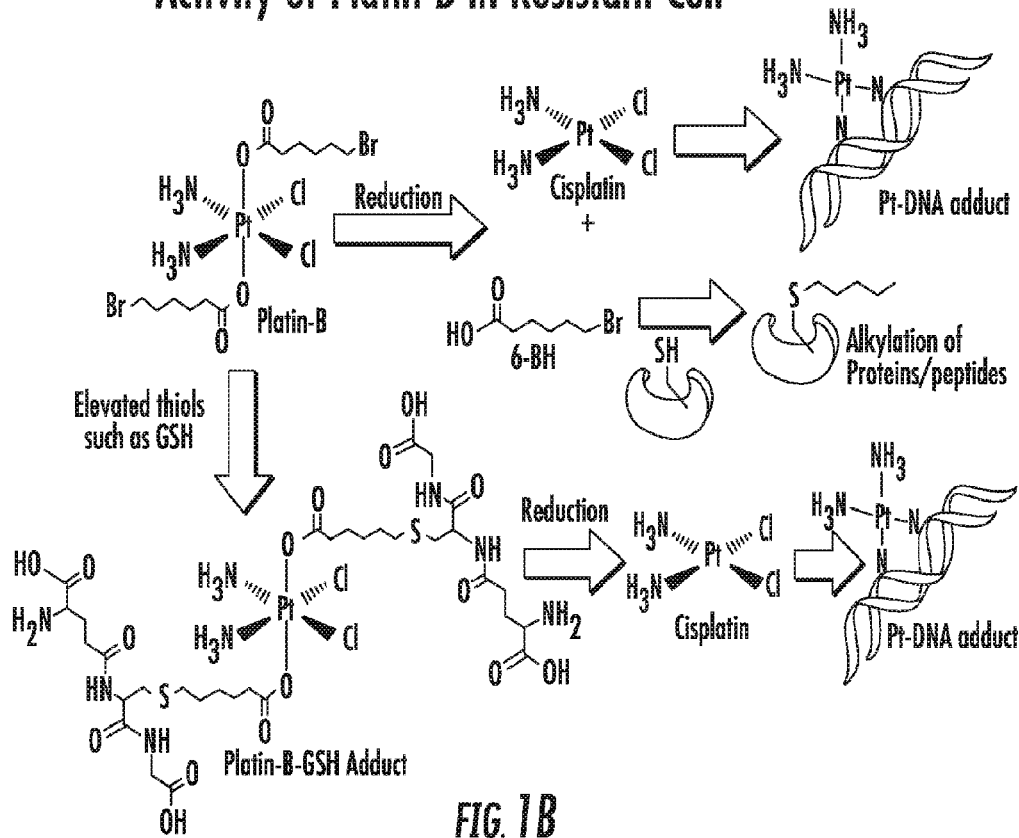
FIG. 1B is a schematic showing Pt(IV) prodrug Platin-B to release cisplatin and an alkylating agent 6-bromohexanoic acid (6-BH) together in one molecular system to overcome resistance.

Intrinsic and acquired cisplatin resistances arise from reduced cellular accumulation of cisplatin, increased expression of intracellular thiols, such as GSH and metallothionein, and repair of Pt-DNA adducts. Thus, disclosed herein are Pt(IV) prodrugs that can circumvent at least one of these mechanisms of resistance. These compounds can also release an alkylating agent, such as 6-BH. The disclosed compounds thus combine an alkylating agent with cisplatin or other platinum containing anti-cancer agent in the form of a single prodrug and to use the ability of the alkylating agent to protect the early sequestration/detoxification of the Pt drug from biological thiols (see e.g., FIG. 1B).

More particularly, kinetically 'inert' Pt(IV) prodrugs can produce active Pt(II) species upon cellular reduction, and thus combat resistance and side effects (Wilson et Chem. Rev., 2014, 114:4470-4495; Dhar et al., J. Am. Chem. Soc., 2009, 131:14652-14653; Dhar et al, Proc. Natl. Acad. Sci. USA, 2011, 108:1850-1855; Dhar et al., Proc. Natl. Acad. Sci. USA, 2009, 106:22199-22204; and Graf et al., Adv. Drug Deliv. Rev., 2012, 64:993-1004). Moreover, the Pt(IV) skeleton provides an opportunity to install additional therapeutic modalities on the axial positions (Pathak et al., Chem. Eur. J., 2014, 20:6861-6865; Pathak et al., Angew. Chem. Int. Ed. Engl., 2014, 53:1963-1967).

Furthermore, GSH is implicated in the regulation of drug efflux in GS-X pump and multi drug resistance-associated protein (MRP)-overexpressing tumor cell lines and in DNA repair (Kuo, Antioxid. Redox Signal., 2009, 11:99-133). Thus, reactivity of alkylating agents from the disclosed prodrugs with GSH can be a key to improve response in resistant tumors. example, an anhydride of 6-BH was synthesized and reacted with c,c,t-[Pt(NH$_3$)$_2$Cl$_2$(OH)$_2$] to get dual characteristics drug modalities Platin-B (Scheme 1). In addition to the alkylating nature, 6-BH moiety also contributes in increasing the lipophilicity of the Pt(IV) drug, which can help in better internalization.

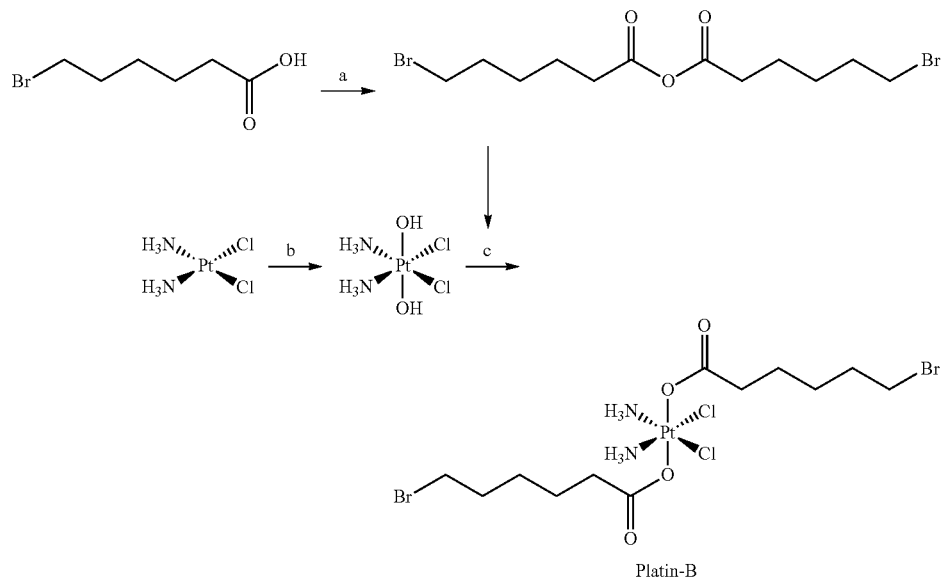

Scheme 1. Synthesis of Platin-B from cisplatin and 6-BH. A) DCC, CH$_2$Cl$_2$, 25° C., 12 h, quantitative yield; b) H$_2$O$_2$, 75° C., 5 h, 90%; c) DMF, 25° C., 12 h, 64%.

Disclosed herein are compounds of Formula I:

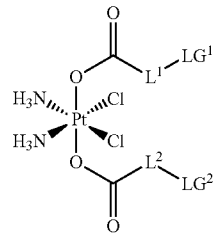

Formula I wherein L$^1$ and L$^2$ are each linker moieties and LG$^1$ and LG$^2$ are each electrophilic leaving group moieties. In Formula 1, L$^1$ and L$^2$ can be the same or different. In Formula I, LG$^1$ and LG$^2$ can be the same or different.

Linkers

The linker moieties L$^1$ and L$^2$ can be from 1 to 24 atoms in length. For example, the linker moieties L$^1$ and L$^2$ can be from 1, 2, 3, 4, 5, 7, 8, 9, 10, 11, 12, 13, 14, 15, 16, 17, 18, 19, 20, 21, 22, 23, or 24 atoms in length, where any of the stated values can form an upper and/or lower end point of a range. In specific examples, L$^1$ and/or L$^2$ can be from 1 to 10, from 10 to 20, from 5 to 15, from 1 to 5, or from 5 to 10 atoms in length. In more specific examples, $L^1$ and/or $L^2$ can be 5 atoms in length. In one specific example, $L^1$ and $L^2$ are both 5 atoms in length.

In certain examples, $L^1$ and/or $L^2$ can be substituted or unsubstituted alkyl. For example, $L^1$ and/or $L^2$ can be an unsubstituted $C_1$-$C_{24}$ alkyl, represented by the formula —$(CH_2)_n$—, where n is 1-24. Examples of where both $L^1$ and $L^2$ are unsubstituted $C_1$-$C_{24}$ alkyl are shown in Formula IA, with n=1-24.

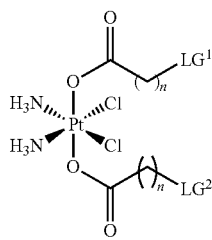

Formula IA

More specific examples include where $L^1$ and/or $L^2$ are —$(CH_2)_n$—, where n is 1-10, 1-5, 5-10, 10-15, or 10-24. Other examples include —$(CH_2)_n$—, where n is 1, 2, 3, 4, 5, 6, 7, 8, 9, 10, 11, 12, 13, 14, 15, 16, 17, 18, 19, 20, 21, 22, 23, or 24, where any of the stated values can form an upper and/or lower end point of a range. Specific examples of such linker moieties include methylene, ethylene, n-propylene, n-butylene, pentylene, hexylene, heptylene, octylene, nonylene, decylene, dodecylene, tetradecylene, hexadecylene, eicosyllene, and tetracosylene. In one specific example $L^1$ and/or $L^2$ are both butylene.

In other examples, $L^1$ and/or $L^2$ can be a substituted $C_1$-$C_{24}$ alkyl, represented by the formula —$(CR^1R^2)_n$—, where n is 1-24, and $R^1$ and $R^2$ are independently chosen from hydrogen, $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or together form a ketone. Examples of where both $L^1$ and $L^2$ are substituted $C_1$-$C_{24}$ alkyl shown in Formula IB, with n=1-24.

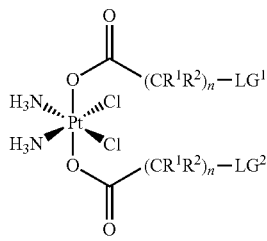

Formula IB

Other examples include where $L^1$ is an unsubstituted $C_1$-$C_{24}$ alkyl and $L^2$ is a substituted $C_1$-$C_{24}$ alkyl.

In still further examples, $L^1$ and/or $L^2$ can be a substituted or unsubstituted $C_1$-$C_{24}$ heteroalkyl where one or more of the carbon atoms in the chain are replaced by an oxygen (e.g., an ether), sulfur (e.g., a thioether), or an amino group. For example, suitable linker moieties can include a methoxymethylene, methoxyethylene, methoxypropylene, methoxybutylene, ethoxymethylene, ethoxyethylene, ethoxypropylene, propoxymethylene, propoxyethylene, methylaminomethylene, methylaminoethylene, methylaminopropylene, methylatninobutylene, ethylaminomethylene, ethylatninoethylene, ethylaminopropylene, propylaminomethylene, propylaminoethylene, methoxymethoxymethylene, ethoxymethoxymethylene, methoxyethoxymethylene, methoxymethoxyethylene, and the like, and derivatives thereof, any of which is optionally substituted with $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or ketone.

In still other examples, $L^1$ and/or $L^2$ can be substituted or unsubstituted $C_{5-10}$ cycloalkyl. For example, $L^1$ and/or $L^2$ can be cyclopentylene, cyclohexylene, cycloheptylene, or cyclooctylene. When substituted, the cycloalkyl group can be substituted with one or more groups including, but not limited to, $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or ketone.

In still other examples, $L^1$ and/or $L^2$ can be substituted or unsubstituted $C_{5-10}$ heterocycloalkyl. For example, $L^1$ and/or $L^2$ can be substituted or unsubstituted piperazinyl, pyrrolidinyl, piperidinyl, morpholinyl, thiomorpholinyl, tetrahydrofuranyl, tetrahydrothiofuranyl, tetrahydropyranyl, and oxanyl. When substituted, the heterocycloalkyl group can be substituted with one or more groups including, but not limited to, $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or ketone.

In further examples, $L^1$ and/or $L^2$ can be substituted or unsubstituted alkenyl. For example, $L^1$ and/or $L^2$ can be $C_2$-$C_{24}$ alkenyl. Specific examples of unsubstituted $C_2$-$C_{24}$ alkenyl linker moieties include —$(CH_2)_a(CH=CH)_b(CH_2)_c$—, where a, b, and c are independently selected from 0-5, 0-10, 0-24, 1-5, 1-10, 1-15, 1-10, 1-5, 5-10, 10-15, or 10-24, wherein b is not 0. Other examples include where a is 0, 1, 2, 3, 4, 5, 6, 7, 8, 9, 10, 11, 12, 13, 14, 15, 16, 17, 18, 19, 20, 21, 22, 23, or 24, bis 1, 2, 3, 4, 5, 6, 7, 8, 9, 10, 11, 12, 13, 14, 15, 16, 17, 18, 19, 20, 21, 22, 23, or 24, and c is 0, 1, 2, 3, 4, 5, 6, 7, 8, 9, 10, 11, 12, 13, 14, 15, 16, 17, 18, 19, 20, 21, 22, 23, or 24, where any of the stated values can form an upper and/or lower end point of a range. Specific examples of alkenyl $L^1$ and/or $L^2$ can be propenylene, butenylene, pentenylene, hexenylene, heptenylene, octenylene, linolenylene, linoleylene, arachidonylene, stearidonylene, eicosapentaenylene, docosahexaenylene, and the like. The E or Z isomers can be used of any of these alkylenes can be used. Specific examples of substituted $C_2$-$C_{24}$ alkenyl linker moieties include —$(CR^1R^2)_a(CR^1=CR^2)_b(CR^1R^2)_c$—, where a, b, and c are as defined before and $R^1$ and $R^2$ are independently chosen from hydrogen, $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or together form a ketone.

In still other examples, $L^1$ and/or $L^2$ can be substituted or unsubstituted $C_{5-10}$ cycloalkyenyl. For example, $L^1$ and/or $L^2$ can be cyclopentenylene, cyclohexenylene, cycloheptenylene, cyclooctenylene, cyclopentadienylene, cyclohexadienylene, cycloheptadienylene, or cyclooctadienylene. When substituted, the cycloalkenyl group can be substituted with one or more groups including, but not limited to, $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or ketone.

In still other examples, $L^1$ and/or $L^2$ can be substituted or unsubstituted $C_{5-10}$ heterocycloalkenyl. For example, $L^1$ and/or $L^2$ can be substituted or unsubstituted pyrrolyl, furanyl, thiophenyl, or pyranyl. When substituted, the heterocycloalkenyl group can be substituted with one or more groups including, but not limited to, $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or ketone.

In further examples, $L^1$ and/or $L^2$ can be substituted or unsubstituted alkynyl. For example, $L^1$ and/or $L^2$ can be $C_2$-$C_{24}$ alkynyl. Specific examples of unsubstituted. $C_2$-$C_{24}$ alkynyl linker moieties include —$(CH_2)_a(C≡C)_b(CH_2)_c$—, where a, b, and c are independently selected from 0-5, 0-10, 0-24, 1-5, 1-10, 1-15, 1-10, 1-5, 5-10, 10-15, or 10-24, wherein b is not 0. Other examples include where a is 0, 1, 2, 3, 4, 5, 6, 7, 8, 9, 10, 11, 12, 13, 14, 15, 16, 17, 18, 19, 20, 21, 22, 23, or 24, b is 1, 2, 3, 4, 5, 6, 7, 8, 9, 10, 11, 12, 13, 14, 15, 16, 17, 18, 19, 20, 21, 22, 23, or 24, and c is 0, 1, 2, 3, 4, 5, 6, 7, 8, 9, 10, 11, 12, 13, 14, 15, 16, 17, 18, 19, 20, 21, 22, 23, or 24, where any of the stated values can form an upper and/or lower end point of a range. Specific examples of substituted $C_2$-$C_{24}$ alkenyl linker moieties include —$(CR^1R^2)_a(C≡C)_b(CR^1R^2)_c$—, where a, b, and c are as defined before and $R^1$ and $R^2$ are independently chosen from hydrogen, $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or together form a ketone.

In other examples, $L^1$ and/or $L^2$ can be a substituted or unsubstituted aryl group. Exemplary aryl groups with six membered rings include benzene or benzene substituted by one or more substituents each independently chosen from $C_1$-$C_{24}$ alkyl, halogenated alkyl, $C_1$-$C_{24}$ alkoxy, $C_2$-$C_{24}$ alkenyl, $C_2$-$C_{24}$ alkynyl, aryl, heteroaryl, amino, carboxylic acid, alkyl ester, halide, hydroxyl, nitro, or ketone. Examples of suitable aromatic linker moieties include benzene, cymene, tetramethylbenzene, hexamethylbenzene, t-butylbenzene, 1,3-diethylbenzene, 1,4-diethylbenzene, toluene and xylene. Exemplary aromatic groups with five membered rings include cyclopentadienyl, substituted cyclopentadienyl, indenyl or substituted indenyl and fluorenyl or substituted fluorenyl.

In other examples, $L^1$ and/or $L^2$ can be a substituted or unsubstituted heteroaryl group. Exemplary heteroaryl groups include pyrimidyl, indolyl, and the like.

Leaving Group

In the disclosed prodrugs $LG^1$ and $LG^2$ are electrophilic leaving groups. These groups can react with nucleophiles on DNA and thereby form vulnerable adducts. Thus, the combined —OC(O)-L-LG moiety in the disclosed prodrugs can act as a DNA alkylating agent. Alkylating agents such as alkyl sulfonates, nitrosoureas, and nitrogen mustards are used for the treatment of solid tumors. They can alkylate essential biological macromolecules, such as thiol groups of protein/peptide and N7 position of guanine bases of DNA. Incorporating such functionality in the disclosed Pt(IV) prodrugs (at $LG^1$ and $LG^2$) can also protect cisplatin and other platinum containing anti-cancer agents from early sequestration and detoxification.

In the disclosed prodrugs, $LG^1$ and $LG^2$ can be the same or different. In certain examples, $LG^1$ and/or $LG^2$ can be Cl, Br, or I. In other examples $LG^1$ and/or $LG^2$ can be tosylate, mesylate, and triflate. In still other examples $LG^1$ and/or $LG^2$ can be alkoxyl, $PF_6$, $BF_4$, $B(ArF)_4$, $ClO_4$, $SbF_6$, $SO_4H$, trifluoroacetate, or thiocyanates. In some examples, $LG^1$ and/or $LG^2$ is Br, which is found in, and thus mimics, pipobroman, a DNA alkylating agent.

In some examples, $LG^1$ and/or $LG^2$ can be a nitrogen mustard. For example, $LG^1$ and/or $LG^2$ can N,N-bis(2-chloroethyl)aniline group. This group is found on chlorambucil, 4-[bis(2-chlorethyl)amino]benzenebutanoic acid, a nitrogen mustard alkylating agent used in the treatment of certain cancers. It is also found in melphalan, 4-[bis(chloroethyl)amino]phenylalanine, another alkylating agent. The N,N-bis(2-chloroethyl)aniline group is shown below:

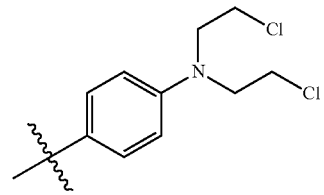 [SMILES: *c1ccc(N(CCCl)CCCl)cc1]

In other examples, $LG^1$ and/or $LG^2$ can be a bis(2-chloroethyl)amine, which is found in chlormethine, bis(2-chloroethyl)methylamine. In other examples, $LG^1$ and/or $LG^2$ can be a N,N-bis(2-chloroethyl)-1-methyl-1H-benzo[d]imidazol-5-amine, which is found in bendamustine, 4-[5-[bis(2-chloroethyl)amino]-1-methylbenzimidazol-2-yl]butanoic acid. In other examples, $LG^1$ and/or $LG^2$ can be a 5-[bis(2-chloroethyl)amino]-1H-pyrimidine-2,4-dione group, which is found in uramustine, 1,3-Bis(2-chloroethyl)-1-nitrosourea, which is found in carmustine, or N-(2-chloroethyl)-N'-cyclohexyl-nitrosourea, which is found in lomustine.

In some examples, $LG^1$ and/or $LG^2$ can be a $C_1$-$C_{24}$ alkyl alkyl sulfonate, —$OSO_2R^3$, where $R^3$ is a substituted or unsubstituted $C_1$-$C_{24}$ alkyl group. Alkyl sulfonates such as busulfan, butane-1,4-diyl dimethanesulfonate, are used as alkylating agents to treat some cancers.

In still other examples, $LG^1$ and/or $LG^2$ can be busulfan, carmustine (BCNU), semustine, chlorambucil, chlorozotocin, cyclophosphamide, ifosphamide, mechlorethamine, melphalan, mitomycin C, procarbazine, streptozotocin, temozolamide, thiotepa, triethylenemelamine, altretamine, or dacarbazine. In still other examples, $LG^1$ and/or $LG^2$ can be an ethylnimines such as thiotepa or triazenes such as decarbazine.

ADDITIONAL EXAMPLES

Also disclosed herein are prodrugs of carboplatin. These are shown in Formula II:

Formula II

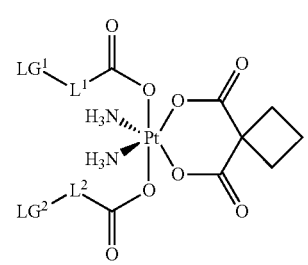

wherein $L^1$, $L^2$, $LG^1$, and $LG^2$ can be as defined herein in for Formula I.

Also disclosed herein are prodrugs of oxaliplatin. These are shown in Formula III:

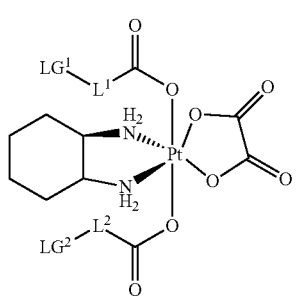

Formula III wherein $L^1$, $L^2$, $LG^1$, and $LG^2$ can be as defined herein in for Formula I.

Also disclosed herein are prodrugs shown in Formulas IV, and VI:

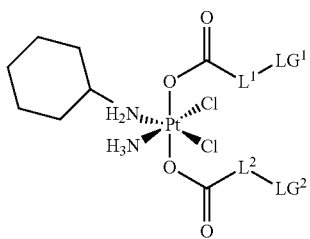

Formula IV

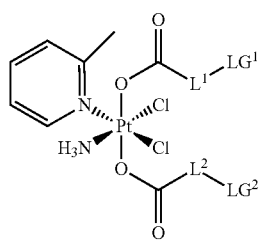

Formula V

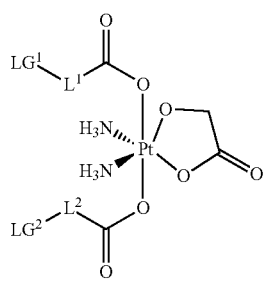

Formula VI wherein $LG^1$, $L^2$, $LG^1$, and $LG^2$ can be as defined herein in for Formula I.

In one specific example, the disclosed prodrug can have the Formula IA-1 (Platin-B) or Formula IA-2 (Platin-Cbl),

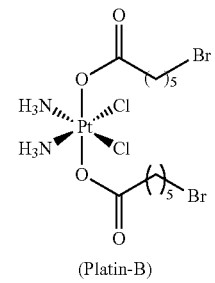

Formula IA-1

(Platin-B)

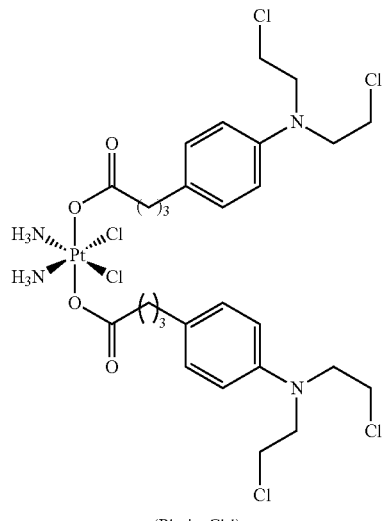

Formula IA-2

(Platin-Cbl)

To demonstrate the utility of a combination of an alkylating agent with cisplatin in the form of a single prodrug, a 6-bromohexanoic acid (6-BH) derivatized Pt(IV) prodrug, Platin-B was developed to attack multiple cellular pathways using alkylating and crosslinking capabilities (FIG. 19). Platin-B allowed delivery of the potent anticancer drug, cisplatin and a mimic of an alkylating agent, 6-BH, in the reducing cancerous cell milieu by detachment of the axial bonds during reduction of Pt(IV) to Pt(II) species. The pipobroman mimicking alkylating agent 6-BH acts against cellular GSH and thus protect the cisplatin center from deactivation by elevated cellular thiols present in resistant cancer cells. Platin-B demonstrated significantly high cytotoxicity profile as compared to cisplatin and its mixture with 6-BH even when it is a Pt(IV) prodrug. GSH modulates cisplatin therapeutic activity by inactivating Pt drugs through direct binding, quenching of monoadducts, and increasing DNA repair activity, thus protection of Platin-B through the Br moieties from GSH induced deactivation can play myriad roles where Platin-B will be able to overcome resistance compared to other similar Pt-based compounds.

Method of Making

The disclosed prodrugs can be produced beginning with the particular platinum anti-cancer agent of choice (e.g., cisplatin, carboplatin, oxaliplatin). These compounds can be oxidized with hydrogen peroxide at elevated temperatures. The oxidized product can then be treated with an activated form of the alkylating moiety (—OC(O)-L-LG) in a suitable solvent (e.g., DMSO, DMF) at around ambient temperature. Various activated forms of the alkylating moieties can be prepared. For example, preparing a terminally LG functionalized carboxylic acid can be performed by methods known in the art. These can then be converted in to anhydrides, mixed anhydrides, or activated esters according to standard techniques.

Pharmaceutical Compositions

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in bacterial enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Nanoparticles

The disclosed compounds can be incorporated into nanoparticles. Suitable nanoparticles include a core and one or more of the compounds disclosed herein. The disclosed compounds can be contained or embedded within the core. The disclosed compounds are preferably released from the core at a desired rate. The core is biodegradable and releases the disclosed compounds as the core is degraded or eroded. The nanoparticles can also comprise a targeting moiety that is available for interaction with cellular components, which interactions will target the nanoparticles to the appropriate cells, such as apoptotic cells; organelles, such as mitochondria; or the like.

The core of the nanoparticle can be formed from any suitable component or components. Preferably, the core is formed from hydrophobic components such as hydrophobic polymers or hydrophobic portions or polymers or lipids. In certain examples, the core includes phospholipids which can form micelles having a hydrophobic core and a hydrophilic outer surface. The core can also or alternatively include block copolymers that have hydrophobic portions and hydrophilic portions that can self-assemble in an aqueous environment into particles having the hydrophobic core and a hydrophilic out surface. In certain examples, the core comprises one or more biodegradable polymer or a polymer having a biodegradable portion.

Any suitable synthetic or natural biodegradable polymers can be used. Such polymers are recognizable and identifiable by one or ordinary skill in the art. Non-limiting examples of synthetic, biodegradable polymers include: poly(amides) such as poly(amino acids) and poly(peptides); poly(esters) such as polylactic acid), poly(glycolic acid), polylactic-co-glycolic acid) (PLGA), and poly(caprolactone); poly(anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), fibrin, fibrinogen, cellulose, starch, collagen, and hyaluronic acid, copolymers and mixtures thereof. The properties and release profiles of these and other suitable polymers are known or readily identifiable.

In various examples, the core comprises PLGA. PLGA is a well-known and well-studied hydrophobic biodegradable polymer used for the delivery and release of therapeutic agents at desired rates.

At least some of the polymers used to form the core are amphiphilic having hydrophobic portions and hydrophilic portions. The hydrophobic portions can form the core, while the hydrophilic regions can for a shell that helps the nanoparticle evade recognition by the immune system and enhances circulation half-life. Examples of amphiphilic polymers include block copolymers having a hydrophobic block and a hydrophilic block. In various examples, the core is formed from hydrophobic portions of a block copolymer, a hydrophobic polymer, or combinations thereof.

Any suitable hydrophilic polymer can form a hydrophilic block of a block copolymer. Examples of suitable hydrophilic polymers include polysaccharides, dextran, chitosan, hyaluronic acid, and the like. In embodiments, polyethylene glycol (PEG) is a hydrophilic polymer used to serve as the hydrophilic portion of a block copolymer.

Nanoparticles, as described herein, can be of any suitable size. Generally, the nanoparticles are of a diametric dimension of less than about 999 nanometers, such as less than about 750 nm, less than about 600 nm, less than about 500 nm, less than about 400 nm, less than about 300 nm, or less than about 200 nm. In addition, or alternatively, the nanoparticles can be of a diametric dimension of greater than about 5 nm. In embodiments, the nanoparticles are from about 30 nm to about 300 nm in diameter. In embodiments, the nanoparticles are separated according to size, such as from about 20 nm to about 40 nm, from about 40 nm to about 60 nm, from about 60 nm to about 80 nm, from about 80 nm to about 100 nm, or from about 100 nm to about 150 nm. In specific examples, the nanoparticles can be from 1 to 1000 nm, from 1 to 10 nm, from 10 to 100, or from 100-1000 nm.

Nanoparticles, as described herein, can be synthesized or assembled via any suitable process. Preferably, the nanoparticles are assembled in a single step to minimize process variation. A single step process can include nanoprecipitation and self-assembly. The nanoparticles can be synthesized or assembled by dissolving or suspending hydrophobic components in an organic solvent, preferably a solvent that is miscible in an aqueous solvent used for precipitation. In certain examples, acetonitrile is used as the organic solvent, but any suitable solvent can be used. Hydrophilic components are dissolved in a suitable aqueous solvent, such as water, 4 wt % ethanol, or the like. The organic phase solution can be added drop wise to the aqueous phase solution to nanoprecipitate the hydrophobic components and allow self-assembly of the nanoparticle in the aqueous solvent.

A process for determining appropriate conditions for forming the nanoparticles can be as follows. Briefly, functionalized polymers and phospholipids may be co-dissolved in organic solvent mixtures (in embodiments, the phospholipids or functionalized phospholipids are dissolved in the aqueous solvent). This solution can be added drop wise into hot (e.g., 65° C.) aqueous solvent (e.g., water, 4 wt-% ethanol, etc.), whereupon the solvents will evaporate, producing nanoparticles with a hydrophobic core coated with phospholipids. The phospholipids used at this stage may be a mixture of non-functionalized phospholipids and functionalized phospholipids (e.g., conjugated to targeting moieties) that can also include a hydrophilic polymer component, such as PEG. Once a set of conditions where a high (e.g., >75%) level of compound loading has been achieved, contrast agents or additional therapeutic agents can be included in the nanoprecipitation and self-assembly of the nanoparticles.

The size of the nanoparticle produced can be varied by altering the ratio of hydrophobic core components to amphiphilic shell components. The choice of PEGylated lipids and bilayer forming phoshpholipds can affect resulting nanoparticle size. PEGylated lipids are known to form small micellar structures because of surface tension imposed by the PEG chains. Nanoparticle size can also be controlled by changing the polymer length, by changing the mixing time, and by adjusting the ratio of organic to the phase. Prior experience with nanoparticles from PLGA-b-PEG of different lengths suggests that NP size will increase from a minimum of about 20 nm for short polymers (e.g., PLGA3000-PEG750) to a maximum of about 150 nm for long polymers (e.g., PLGA1000,000-PEG-10,000). Thus, molecular weight of the polymer will serve to adjust the size.

Nanoparticle surface charge can be controlled by mixing polymers with appropriately charged end groups. Additionally, the composition and surface chemistry can be controlled by mixing polymers with different hydrophilic polymer lengths, branched hydrophilic polymers, or by adding hydrophobic polymers.

Once formed, the nanoparticles can be collected and washed via centrifugation, centrifugal ultrafiltration, or the like. If aggregation occurs, nanoparticles can be purified by dialysis, can be purified by longer centrifugation at slower speeds, can be purified with the use surfactant, or the like.

Once collected, any remaining solvent can be removed and the particles can be dried, which should aid in minimizing any premature breakdown or release of components. The nanoparticles can be freeze dried with the use of bulking agents such as mannitol, or otherwise prepared for storage prior to use.

The disclosed compounds can be incorporated into liposomes. As is known in the art, liposomes are generally derived from phospholipids or other lipid substances.

Liposomal Formulations

The disclosed compounds can also be formulated into liposomes. Liposomes can be formed by mono- or multi-lamellar hydrated liquid crystals that are dispersed in an aqueous medium. Any non-toxic, physiologically acceptable and metabolizable lipid capable of forming liposomes can be used. The disclosed compounds in liposome form can contain, in addition to a compound as disclosed herein, stabilizers, preservatives, excipients, and the like. Examples of suitable lipids are the phospholipids and the phosphatidyl cholines (lecithins), both natural and synthetic. Methods of forming liposomes are known in the art. See, e.g., Prescott, Ed., Methods in Cell Biology, Volume XIV, Academic Press, New York, p. 33 et seq., 1976, which is hereby incorporated by reference herein for its teachings of liposomes and their preparation.

In other examples, the liposomes can be cationic liposomes (e.g., DOTMA, DOPE, DC cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see e.g., Brigham et al, Am. J. Resp. Cell. Mol. Biol. 1989, 1:95-100; Feigner et al., Proc. Natl. Acad. Sci. USA 1987, 84:7413-7; and U.S. Pat. No. 4,897,355, which are incorporated by reference herein for their teachings of liposomes. As one example, delivery can be via a liposome using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures, standard in the art. Liposomes where the diffusion of the compound or delivery of the compound from the liposome is designed for a specific rate or dosage can also be used.

As described herein, niosomes are delivery devices that can be used to deliver the disclosed compositions. Noisomes are multilamellar or unilamellar vesicles involving nonionic surfactants. An aqueous solution of solute is enclosed by a bilayer resulting from the organization of surfactant macromolecules. Similar to liposomes, noisomes are used in targeted delivery of, for example, anticancer drugs. They are generally understood to be different from transfersomes, vesicles prepared from amphiphilic carbohydrate and amino group containing polymers, e.g., chitosan, which can also be used to formulate a compound as disclosed herein.

Nanoerythrosomes are delivery devices that can be used to deliver the disclosed compounds. Nanoerythrosomes are nano-vesicles made of red blood cells via dialysis through filters of defined pore size. These vesicles can be loaded with a diverse array of biologically active molecules, including proteins and the compounds disclosed herein. They generally serve as ideal carriers for antineoplastic agents.

Microcapsules

Microcapsules are further delivery devices that can be used to deliver the disclosed compositions. In contrast to liposomal delivery systems, microspheres and micro-capsules typically do not have an aqueous core but a solid polymer matrix or membrane. These delivery devices are obtained by controlled precipitation of polymers, chemical crosslinking of soluble polymers, and interfacial polymerization of two monomers or high-pressure homogenization techniques. The encapsulated compound is gradually released from the depot by erosion or diffusion from the particles. Poly(lactide co-glycolide) (PLEA) microspheres are currently used as monthly and three monthly dosage forms in the treatment of cancer.

Methods of Use

Provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma. Treatment of breast cancer by administering the disclosed compounds is particularly preferred.

Cancers that are preferably treated by the disclosed methods using the compounds disclosed herein are lung, breast, brain, ovarian, lymphoma, leukemia, head and neck, pancreatic, and cervical, colon and rectum, endometrial, esophagus, liver, penile, skin-melanoma, skin-nonmelanoma, stomach, testicular, vaginal, uterine, vulvar, paranasal cancer, oropharyngeal and laryngeal cancers.

The methods of treatment or prevention described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine water, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, Erwinia L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, II 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, isotretinoin, Kidrolase, Lanacort, L-asparaginase, and LCR. The additional anti-cancer agent can also include biopharmaceuticals such as, for example, antibodies.

In further examples, the disclosed compounds can be combined with (in the same composition, co-administered, or administered as part of a treatment regimen) Sipuleucel-T (Provenge), Alemtuzumab, Bevacizumab, Brentuximab vedotin, Cetuximab, Gemtuzumab ozogamicin, Ibritumomab tiuxetan, Ipilimumab, Ofatumumab, Panitumumab, Rituximab, Tositumomab, or Trastuzumab. In further examples, the disclosed compounds can be combined with (in the same composition, co-administered, or administered as part of a treatment regimen) interleukin-2 and interferon-α.

In certain examples, the disclosed compounds can be combined with Telcyta.

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation. An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The disclosed compounds can also be used to treat inflammatory and autoimmune disorders or conditions such as, but are not limited to, systemic lupus erythematosus, Hashimoto's disease, rheumatoid arthritis, gouty arthritis, graft-versus-host disease, Sjögren's syndrome, pernicious anemia, Addison disease, scleroderma, Goodpasture's syndrome, inflammatory bowel diseases such as Crohn's disease, colitis, atypical colitis, chemical colitis; collagenous colitis, distal colitis, diversion colitis: fulminant colitis, indeterminate colitis, infectious colitis, ischemic colitis, lymphocytic colitis, microscopic colitis, gastroenteritis, Hirschsprung's disease, inflammatory digestive diseases, Morbus Crohn, non-chronic or chronic digestive diseases, non-chronic or chronic inflammatory digestive diseases; regional enteritis and ulcerative colitis, autoimmune hemolytic anemia, sterility, myasthenia gravis, multiple sclerosis, Basedow's disease, thrombopenia purpura, insulin-dependent diabetes mellitus, allergy; asthma, atopic disease; arteriosclerosis; myocarditis; cardiomyopathy; glomerular nephritis; hypoplastic anemia; rejection after organ transplantation and numerous malignancies of lung, prostate, liver, ovary, cervix, lymphatic and breast tissues, psoriasis, acne vulgaris, asthma, autoimmune diseases, celiac disease, chronic prostatits, glomerulonephritis, inflammatory bowel diseases, pelvic inflammatory disease, reperfusion injury sarcoidosis, vasculitis, interstitial cystitis, type 1 hypersensitivities, systemic sclerosis, dermatomyositis, polymyositis, and inclusion body myositis.

In one embodiment, an effective amount of one or more compounds or compositions disclosed herein is administered to a subject having an inflammatory or autoimmune disorder and who is in need of treatment thereof. The disclosed methods can optionally include identifying a subject who is or can be in need of treatment of an inflammatory or autoimmune disorder. The subject can be a human or other mammal, such as a primate (monkey, chimpanzee, ape, etc.), dog, cat, cow, pig, horse, mouse or other animals having an inflammatory disorder. Means for administering and formulating compounds for administration to a subject are known in the art, examples of which are described herein.

Also disclosed is a method for treating a subject having a neurodegenerative disease or disorder. As used herein, "neurodegenerative disease" includes neurodegenerative disease associated with protein aggregation, also referred to as "protein aggregation disorders", "protein conformation disorders", or "proteinopathies". Neurodegenerative disease associated with protein aggregation include diseases or disorders characterized by the formation of detrimental intracellular protein aggregates (e.g., inclusions in the cytosol or nucleus) or extracellular protein aggregates (e.g., plaques). "Detrimental protein aggregation" is the undesirable and harmful accumulation, oligomerization, fibrillization or aggregation, of two or more, hetero- or homomeric, proteins or peptides. A detrimental protein aggregate may be deposited in bodies, inclusions or plaques, the characteristics of which are often indicative of disease and contain disease-specific proteins. For example, superoxide dismutase-1 aggregates are associated with ALS, poly-Q aggregates are associated with Huntington's disease, and α-synuclein-containing Lewy bodies are associated with Parkinson's disease.

Neurological diseases are also associated with immune failure related to increasing levels of disease-causing factors that exceed the ability of the immune system to contain, or a situation in which immune function deteriorates or is suppressed concomitantly with disease progression, due to factors indirectly or directly related to the disease-causing entity. MDSCs can cause T-cell deficiency by suppressing effector T cell activity, thus promoting neurodegenerative disease associated with immune failure.

Representative examples of Protein Aggregation Disorders or Proteopathies include Protein Conformational Disorders, Alpha-Synucleinopathies, Polyglutamine Diseases, Serpinopathies, Tauopathies or other related disorders. Other examples of neurological diseases or include, but are not limited to, Amyotrophic Lateral Sclerosis (ALS), Huntington's Disease (HD), Parkinson's Disease (PD), Spinal Muscular Atrophy (SMA), Alzheimer's Disease (AD), diffuse Lewy body dementia (DLBD), multiple system atrophy (MSA), dystrophia myotonica, dentatorubro-pallidoluysian atrophy (DRPLA), Friedreich's ataxia, fragile X syndrome, fragile XE mental retardation, Machado-Joseph Disease (MJD or SCA3), spinobulbar muscular atrophy (also known as Kennedy's Disease), spinocerebellar ataxia type 1 (SCA1) gene, spinocerebellar ataxia type 2 (SCA2), spinocerebellar ataxia type 6 (SCA6), spinocerebellar ataxia type 7 (SCA7), spinocerebellar ataxia type 17 (SCA17), chronic liver diseases, familial encephalopathy with neuroserpin inclusion bodies (FENIB), Pick's disease, corticobasal degeneration (CBD), progressive supranuclear palsy (PSP), amyotrophic lateral sclerosis/parkinsonism dementia complex, Cataract, serpinopathies, haemolytic anemia, cystic fibrosis, Wilson's Disease, neurofibromatosis type 2, demyelinating peripheral neuropathies, retinitis pigmentosa, Marfan syndrome, emphysema, idiopathic pulmonary fibrosis, Argyophilic grain dementia, corticobasal degeneration, diffuse neurofibrillary tangles with calcification, frontotemporal dementia/parkinsonism linked to chromosome 17, Hallervorden-Spatz disease, Nieman-Pick disease type C, subacute sclerosing panencephalitis, cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalized dystonia such as iodiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia)]; obesity, bulimia nervosa and compulsive eating disorders; pain including bone and joint pain (osteoarthritis), repetitive motion pain, dental pain, cancer pain, myofacial pain (muscular injury, fibromyalgia) perioperative pain (general surgery, gynecological), chronic pain, neuropathic pain, post-traumatic pain, trigeminal neuralgia, migraine and migraine headache; obesity or eating disorders associated with excessive food intake and complications associated therewith; attention-deficit/hyperactivity disorder; conduct disorder; mood disorders including depressive disorders, bipolar disorders, mood disorders due to a general medical condition, and substance-induced mood disorders; muscular spasms and disorders associated with muscular spasticity or weakness including tremors; urinary incontinence; amyotrophic lateral sclerosis; neuronal damage including ocular damage, retinopathy or macular degeneration of the eye, hearing loss or tinnitus; emesis, brain edema and sleep disorders including narcolepsy, and apoptosis of motor neuron cells. Illustrative examples of the neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine. The neuropathic pain includes the pain caused by either central or peripheral nerve damage. And it includes the pain caused by either mononeuropathy or polyneuropathy.

Further provided herein are methods of treating anemia of chronic disease (including cancer-related anemia) in a subject, comprising administering to the subject an effective amount of a compound or composition as disclosed herein.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process.

All chemicals were received and used without further purification unless otherwise noted. Cisplatin was purchased from Strem Chemicals, Inc. 6-Bromohexanoic acid (6-BH), N,N'-dicyclohexylcarbodiimide (DCC), hydrogen peroxide solution (30 wt. % in $H_2O$), and (3-(4,5-dimethylthiazol-2-yl)-2,5-diphenyltetrazolium bromide (MTT) were purchased from Sigma-Aldrich. ALEXA FLUOR™ 488 annexin V/dead cell apoptosis kit was purchased from Invitrogen, Glutathione (GSH), $K_2PtCl_4$, 2'-deoxyguanosine 5'-monophosphate sodium salt hydrate (5'-dGMP), and sodium ascorbate were purchased from Sigma Aldrich. KCl for electrochemistry was purchased from Sigma Aldrich. Glutathione Stransferase (GST) activity assay kit (colorimetric, ab65326) was procured from Abcam. TEHOLTRACKER™ Violet (glutathione detection reagent, catalog number T10095) was obtained from Life Technologies. The mitochondrial DNA isolation Kit (ab65321) and nuclear DNA isolation kit (ab65358) were purchased from Abcam. Bicinchoninic acid (BCA) protein assay kit (Pierce 23227) was purchased from Thermo Scientific. Human hexokinase 2 (HK2, catalog number H2917 Sigma) and bovine serum albumin (BSA, catalog number A2153) were purchased from Sigma Aldrich. Oligomycin, rotenone, antimycin-A, and trifluorocarbonylcyanide phenylhydrazone (FCCP) were purchased from Sigma Aldrich. The protease inhibitor cocktail was purchased from Sigma Aldrich. The Thermo Scientific Mitochondria isolation kit (catalog number 89874) was used to isolate mitochondria, nucleus, and cystosol. Distilled water was purified by passage through a Millipore Milli-Q Biocel water purification system (18.2 MΩ) containing a 0.22 μm filter. $^1H$ and $^{13}C$ spectra were recorded on 400 MHz Varian NMR spectrometer and $^{195}Pt$ NMR spectra were recorded on a 500 MHz Varian NMR spectrometer using $K_2PtCl_4$ as external standard. Plate reader analyses were performed on a Bio-Tek Synergy HT microplate reader. Flow cytometry studies were performed on a BD LSRII flow cytometer equipped with digital acquisition using FACSDiva v6. Electrospray ionization mass spectrometry (ESI-MS) and high-resolution mass spectrometry (HRMS)-ESI were recorded on Perkin Elmer SCIEX API 1 plus and Thermo scientific ORBITRAP ELITE instruments, respectively. Matrix-assisted laser desorption/ionization (MALDI)-time of flight (TOF)-mass spectrometry (MS)

experiments were carried out on a Balker Autoflex (TOF) mass spectrometer. Electrochemical measurements were made at 25° C. on an analytical system model CHI 920c potentiostat from CH Instruments, Inc. (Austin, Tex.). FTIR spectra were collected on a Thermo-Nicolet 6700 spectrophotometer equipped with OMNIC software using samples prepared as pressed KBr pellets. High-performance liquid chromatography (HPLC) analyses were made on an Agilent 1200 series instrument equipped with a multiwavelength UV-visible and a fluorescence detector. Cells were counted using COUNTESS™ Automated Cell Counter procured from invitrogen life technology. Elemental analyses were performed Perkin Elmer 2400 Carbon, Hydrogen Nitrogen (CHN) Analyzer at the Center for Applied isotope Studies at the University of Georgia. Bioenergetic assays were carried out using a Seahorse XF24 analyzer (Seahorse Biosciences, North Billerica, Mass., USA). Inductively coupled plasma mass spectrometry (ICP-MS) studies were performed on a VG PlasmaQuad 3 ICP mass spectrometer. UV-visible measurements were carried out on a Thermo-scientific Nanodrop 2000c instrument.

Human prostate cancer cell line PC3 and DU145 were procured from the American type culture collection (ATCC). Ovarian cancer A2780 cells were obtained from Prof, Robert Brown, Imperial College London. Cisplatin resistant human ovarian carcinoma cell line A2780/CP70 was kindly provided by Thomas Hamilton (Fox Chase Cancer Center, Jenkintown, Pa.). PC3, DU145, and A2780/CP70 cells were grown in Roswell Park Memorial Institute (RPMI) 1640 medium supplemented with 10% fetal bovine serum (FBS) and 1% penicillin/streptomycin 2 mM L-glutamine, and 0.25 units/mL, insulin. Cells were passed every 3 to 4 days and restarted from frozen stocks upon reaching 20 passages.

All data were expressed as mean±S.D (standard deviation). Statistical analysis were performed using GraphPad PRISM™ software v. 5.00. Comparisons between two values were performed using an unpaired Student t test. A one-way ANOVA with a post-hoc Tukey test was used to identify significant differences among the groups.

Synthesis of Anhydride of 6-BH

A suspension of 6-BH (1.0 g, 5.13 mmol) in 15 mL of dry $CH_2Cl_2$ was prepared and a solution of 1,3-dicyclohexylcarbodiimide (DCC) (0.529 g, 2.56 mmol) in 5 mL of $CH_2Cl_2$ was added. The reaction mixture was stirred at room temperature for overnight. The dicyclohexylurea (DCU) was filtered off using glass filter and washed with a small amount of $CH_2Cl_2$. The solvent was evaporated and the resulting residue was resuspended in ethylacetate to precipitate remaining DCU. Residual DCU was removed by filtering the resulting precipitate through a glass filter. The filtrate was evaporated to give anhydride as transparent oil. Yield: Quantitative. Resulting product was used immediately for the next reaction.

Synthesis of c,c,t[$Pt(NH_3)_2Cl_2(OH)_2$]

Hydrogen peroxide (30 wt %, 60 mL) was added drop wise to a round bottom flask containing cisplatin (1.0 g, 3.33 mmol). The reaction mixture was heated to 75° C. for 5 h. The bright yellow solution was kept at room temperature in the dark for overnight to allow crystallization of the product. Yellow crystals were separated by filtration, washed with cold water, and dried to get 1 g of compound c,c,t-[$Pt(NH_3)_2Cl_2(OH)_2$]. Yield 90%. IR (KBr) $v_{max}(cm^{-1})$: 3803 (w), 3515 (w), 3458 (br, OH), 3269 (w), 1582 (s), 1442 (s), 1378 (s), 1074 (m, Pt—OH), 860 (br), 542 [br, Pt—N(O)]. HRMS m/z Calcd. for $Cl_2H_9N_2O_2Pt$: $(W+H)^+$ 333.9689. Found 333.9683. Melting Point: 295-300° C.

Synthesis of Platin-B

A mixture of c,c,t-[$Pt(NH_3)_2Cl_2(OH)_2$] (200 mg, 0.6 mmol) and freshly prepared anhydride of 6-BH (879 mg, 2.4 mmol) in 5 mL dimethylformamide (DMF) was stirred for 16 h at room temperature to get a clear yellow solution. The solvent was evaporated using rotary evaporator under diminished pressure. The crude product was precipitated three times by dissolving in acetonitrile:diethylether (5:45 mL) to get a yellow solid which was isolated though centrifugation (3024×g, 4° C.). Yield 320 mg (78%). $^1$H NMR (DMSO-$d_6$, 400 MHz) ppm: δ 6.52 (broad, 6H), 3.51 (t, 4H), 2.22. (m, 4H), 1.79 (m, 4H), 1.47 (m, 4H), 1.38 (m, 4H). $^{13}$C NMR (DMSO-$d_6$, 100 MHz) ppm: δ 181.06, 35.87, 35, 30, 32.53, 27.58, 24.97. $^{195}$Pt (DMSO-$d_6$, 107.6 MHz) ppm: δ 1230.58. HRMS-ESI m/z Calcd. For $C_{12}H_{27}Br_2Cl_2N_2O_4Pt$: $(M+H^+)$ 685,9362; Found 685.9355. Melting Point: 110-115° C. Elemental analysis % calcd. For $C_{12}H_{26}Br_2Cl_2N_2O_4Pt$: C 20.95, H 3.81, N 4.07; found: C 20.69, H 4.03, N 4.04.

Cyclic Voltammetry

Redox potential of platinum (IV) prodrugs play important roles in regulating efficacy. The disclosed Pt(IV) prodrugs can be activated selectively by intracellular reduction, preferably at the tumor sites to reduce side effects. Redox potential is a measure of the ability of Pt(IV) compounds to form the active platinum (II) species. Electrochemical measurements on Platin-B were carried out in dimethylformamide (DMF)-phosphate buffered saline (PBS) at pH 6.0 and 7.4. Specifically, a conventional three-electrode set-up comprising a glassy carbon working electrode, platinum wire auxiliary electrode, and Ag/AgCl (3M KCl) reference electrode was used for electrochemical measurements. The electrochemical data were uncorrected for junction potentials. KCl was used as a supporting electrolyte. Platin-B (2 mM) solutions were prepared in 40% DMF phosphate buffered saline (PBS) of pH 6.0 and 7.4 with 0.1 M KCl and voltammograms were recorded at different scan rates. The cyclic voltammograms of Platin-B showed Pt(IV)/Pt(II) couple near −0.217 and −0.187 V vs. normal hydrogen electrode (NHE) at pH 7.4 and 6.0, respectively. Thus, Platin-B displayed chemically irreversible two electron reduction due to the detachment of two axial ligands resulting the transformation of Pt(IV) species to the biologically active Pt(II) species. These reduction potential values suggested that Platin-B is susceptible to get reduced in the reducing cellular milieu to produce the active form of drugs.

Titrations of Platin-B with AsA

In order to evaluate reduction of Platin-B to its active Pt(II) form, $^1$H NMR titrations were carried out in presence of ascorbic acid (AsA). Platin-B (10 mg in 500 μL of DMSO-$d_6$) was titrated with different molar ratio of ~300 μL of AsA (1 to 10 equivalents) and spectra were recorded at every 10 min.

Upon reduction, distinct peak corresponding to —$NH_3$ for Pt(IV) prodrugs should shift due to the detachment of the axial ligands to form Pt(II) species. Spectral analyses demonstrated reduction of Platin-B by AsA followed by the release of the axial ligands. Although complete release of axial ligands was not observed in the experimental settings, the changes were significant, which supported reduction of Platin-B by AsA. The peak ~6.5 ppm diminished significantly and a group of three peaks at ~6.9-7.2 ppm characteristics of the reduced species appeared. In the aliphatic region, peaks ~3.5 ppm (shifting up field and down field for the mono-6-BH—Pt(IV) bound and released 6-BH, respectively), 2.2 ppm (triplet becomes a multiplet due to the intact and released 6-BH moiety), the quartet at 1.75 ppm shifted position, and similar shifts were observed for the peak at 1.45 ppm.

Pt-GG Adduct Determination

Platin-B (2.06 mg, 0.003 mM) was dissolved in acetonitrile-water (1:2, 3 mL). To this solution, 5'-GMP (5.20 mg, 0.015 mM) and sodium ascorbate (2.64 mg, 0.015 mM) were added, and the mixture was incubated at 37° C. for 240 h. The deep brown solution was lyophilized. The resulting residue was dissolved in water and analyzed by MALDI-TOF-MS.

Pt(II) compounds such as cisplatin exhibit their anticancer activity due to their inherent proficiency to bind with the N7 position of guanine bases to form crosslinks leading to nuclear DNA damage. Platin-B, a prodrug used for this study was used in simulated cellular reducing environment using sodium ascorbate to investigate the ability of this Pt(IV) compound in producing such adducts with guanosine 5'-monophosphate (5"-dGMP), a truncated base of DNA. Analyses of the products by matrix-assisted laser desorption/ionization (MALDI)-time of flight (TOF)-mass spectrometry (MS) confirmed the presence of following PtII-5'-dGMP-adducts: Pt-GG (m/z=889), Pt-GG($NH_3$) (m/z=906), and [Pt GG($NH_3$)$_2$] (m/z=922).

Interaction of Platin-B with GSH by $^1$H NMR

In order to confirm the adduct formation of Platin-B with GSH, $^1$H NMR titrations were carried out in DMSO-$d_6$. Platin-B (10 mg in 500 μL of DMSO-$d_6$) was titrated with different molar ratio of ~400 μL, of GSH (1 to 10 equivalents).

Figure 2:
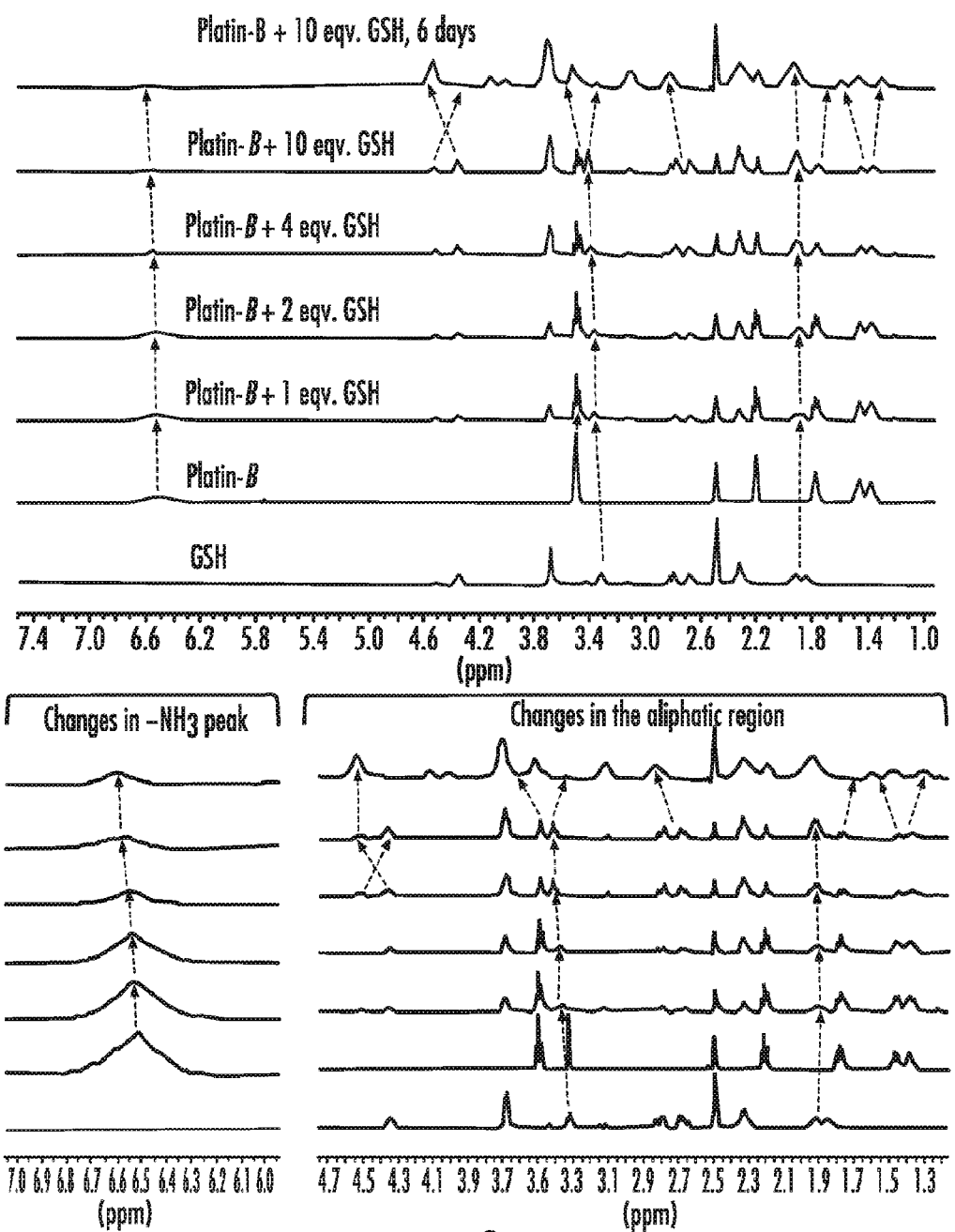
FIG. 2 (top) is the full spectra for the reaction of Platin-B with different equivalents of GSH in DMSO. A significant shift of —$NH_3$ protons confirms an adduct between Platin-B and GSH (bottom left). Aliphatic regions of Platin-B-GSH adduct indicate alteration of chemical shifts of both GSH and Platin-B protons during the titration signifying binding of GSH to Platin-B (bottom right).

The kinetics of competition of Platin-B reduction by GSH versus alkylation of GSH by 6-BH tails from Platin-B using $^1$H spectroscopic analysis was investigated (FIG. 2). The nucleophilic —SH from GSH is expected to interact with the electrophilic —Br moieties in Platin-B to make Platin-B-GSH adduct. $^1$H NMR titrations were carried out at different stoichiometric ration of Platin-B and GSH in a time dependent manner. Resultant spectra demonstrated changes in the chemical shifts of both GSH and Platin-B protons during the titrations supporting binding nature of GSH to Platin-B. Retention of significant shift for the protons of $NH_3$ of Pt(IV) prodrug further confirmed that GSH initially binds to Platin-B through nucleophilic substitution. To validate these interactions, NMR studies were carried out with the isolated Platin-B-GSH adduct and found almost similar pattern of chemical shifts. The $NH_3$ peaks of Pt(IV) were intact and experienced significant changes as found with in situ titrations.

Interaction of Platin-B with GSH by RP-HPLC

The binding ability of Platin-B with GSH was studied by monitoring the reaction of Platin-B (1 mM) and GSH (2 mM) in DMSO by RPHPLC. A 5 μL of the reaction mixture was injected using a Zorbax C18 column and a 60:40 acetonitrile with 1% trifluoroacetic acid:ammonium acetate buffer of pH 7.0 as mobile phase. The wavelength used for these experiments was 255 nm.

The binding ability of Platin-B with GSH was studied by monitoring the reaction of one equivalent of Platin-B and two equivalents of GSH in dimethyl sulfoxide (DMSO) at different time points using RPHPLC. During the course of this reaction, the peak ~14.7 min corresponding to Platin-B decreases and the peaks for Platin-B-GSH adduct at ~9.7 and ~11.45 min increase with time clearly demonstrating Platin-B-GSH adduct formation instead of reduction of Platin-B by GSH.

Platin-B-GSH Adduct by Cyclic Voltammetry

Platin-B (2 mM) solutions were prepared in 40% DMF-PBS of pH 6.0 and 7.4 with 0.1 M KCl and reacted with varied equivalents of GSH and voltammograms were recorded at different scan rates as described above.

At one equivalent of GSH, where it will start forming new species, current-height increased significantly. Upon addition of second equivalent of GSH, current remains same as Platin-B; however, significant shift was observed in the reduction potential indicating formation of relatively stable species. Higher concentration of GSH provided reducing environment in aqueous milieu and contributed in reducing the Platin-B-GSH adduct.

Interaction of Platin-B with GSH by ESI-MS

Platin-B (8.5 mg, 0.013 mmol) and GSH (7.51 mg, 0.025 mmol) were mixed in DMSO. Either dimethyl amino pyridine (DMAP) (3.017 mg, 0.025 mmol) or triethylamine (2.76 mg, 0.025 mmol) was added to this reaction mixture to activate GSH. Reaction was stirred for 16 h and the resulting solution was lyophilized to dryness and analyzed by ESI-MS.

Figure 3:
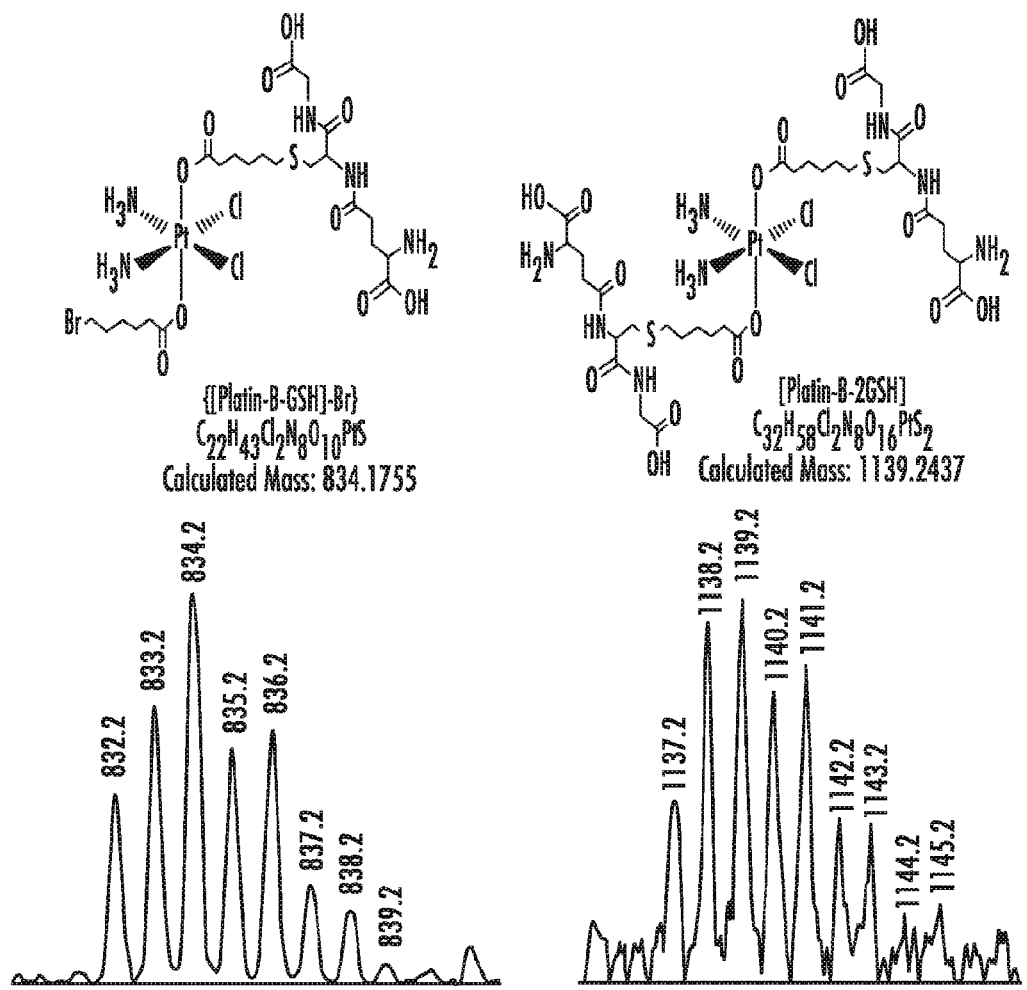
FIG. 3 is a pair of ESI-MS spectra-tecting two Platin-B-GSH adducts forming upon incubation of Platin-B with GSH.

To further validate the results obtained for the Platin-B-GSH adducts from HPLC, electrochemistry and NMR, ESI-MS studies were carried out. Platin-B-GSH (m/z=834.17) and Platin-B-2GSH (m/z=1139.24) adducts were observed by mass spectrometry (FIG. 3). Isotopic peak patterns observed with these two mass peaks showed remarkable similarities with the calculated patterns indicating the Pt containing adducts. Thus, Platin-B interacts with GSH and protects from GSH induced deactivation.

Water-Octanol Partition Coefficient (log P) Determination

Lipophilicity (log P) of Platin-B, butyroplatin, and cisplatin were investigated using water-octanol system. Both octanol and 1×PBS were saturated by mixing a 1:1 mixture at room temperature for overnight. Platin-B or butyroplatin solutions were made in pre-saturated octanol at a concentration of 100 μM. Cisplatin (100 μM) solution was made in 1× PBS. A 0.5 mL octanol solution of the prodrugs (100 μM) was mixed with 0.5 mL of pre-saturated 1×PBS in 1.5 mL in microcentrifuge tubes. For Cisplatin, 100 μM of 0.5 mL 1× PBS was mixed with pre-saturated octanol. These mixed solutions were vigorously shaken in an orbital shaker for 24 h and the two phases were separated by centrifugation followed by quantification of the Pt contents in the water and octanol layers using ICP-MS. Partition coefficient, log P was calculated using the following equation, log P=log([OPt]/[WPt], where OPt stands for the concentration of platinum compounds in octanol and WPt for the concentration of platinum compounds in water.

MTT Assay and Data Analysis

The cytotoxic behaviors of cisplatin, a mixture of cisplatin and 6-BH, and Platin-B were evaluated using the MTT assay against PC3, A2780, and A2780/CP70 cells. Cytotoxic profiles of Platin-B and cisplatin was also assessed in the presence of BSO and GSH by preincubating cells with BSO and GSH (500 μM) while plating the cells. PC3, A2780, or A2780/CP70 cells (2000 cells/well/100 μL) were seeded on a 96-well plate in 100 μL of desired medium and incubated for 24 h. After 24 h, media was removed and fresh media was added. The cells were treated with different constructs at varying concentrations and incubated for 72 h at 37° C. in 5% $CO_2$. The cells were then treated with 20 μL of MTT (5 mg/mL in PBS) for 5 h. The medium was removed, the cells were lysed with 100 μL of DMSO, and the absorbance of the purple formazan was recorded at 550 nm using a Bio-Tek Synergy HT microplate reader. The background absorbance for each well was measured at 800 nm. Each well was performed in triplicate. For studies using high glucose medium, RPMI 1640 media was prepared by adding 1.60 g of glucose for 500 mL of total medium supplemented with 10% FBS and 1% penicillin/streptomycin to have final 28.9 mM of final glucose concentration. Cells were grown for 7 days in high glucose medium prior to the MTT experiment. Cytotoxicity was expressed as mean percentage increase relative to the unexposed control±SD. Control values were set at 0% cytotoxicity or 100% cell viability. Cytotoxicity data was fitted to a sigmoidal curve and a three parameters logistic model used to calculate the $IC_{50}$, which is the concentration of chemotherapeutics causing 50% inhibition in comparison to untreated controls. The mean $IC_{50}$ is the concentration of agent that reduces cell growth by 50% under the experimental conditions and is the average from at least four independent measurements that were reproducible and statistically significant. The $IC_{50}$ values were reported at ±99% confidence intervals. This representative viability assay for Platin-B and related controls in all cells lines are shown in FIG. 4.

For the prostate cancer cell line PC3, which is highly susceptible to get resistance against cisplatin, Platin-B has an $IC_{50}$ value of 1.2±0.2 µM, much lower to that of cisplatin (14.4±1.6 µM). Thus, Platin-B exhibited significantly lower $IC_{50}$ value than cisplatin and even a mixture of cisplatin and two equivalents of 6-BH (11.5±0.7 µM) (Table 1, FIG. 4). A model compound butyroplatin (FIG. 4) with similar structure as Platin-B but devoid of two —Br moieties demonstrated very high $IC_{50}$ values of 26.1±5.8 µM. A very low value of $IC_{50}$ of Platin-B compared to cisplatin even when it is a Pt(IV) prodrug demonstrated its unique and elevated potency for the treatment of cancers recognized with resistance.

A good correlation between the degree of resistance and the increase of the GSH exists. Thus, cisplatin resistant ovarian cancer A2780/CP70 cell line were used as a model of GSH elevated resistant cells and evaluated cytotoxic activities of Platin-B in this cell line (Table 1, FIG. 4). The resistant cells were ~19-fold more resistant to cisplatin ($IC_{50}$=14.7±0.9 µM) than to Platin-B ($IC_{50}$=0.75±0.2 µM). A mixture of cisplatin and two equivalents of 6-BH showed ~14 fold and butyroplatin demonstrated ~44-fold more resistance in these cells compared to Platin-B (Table 1, FIG. 4).

TABLE 1

$IC_{50}$ (µM) of cisplatin, 6-BH, a mixture of cisplatin and 6-BH, and Platin-B in different cell lines

|  | PC3 | A2780 | A2780/CP70 |
| --- | --- | --- | --- |
| Cisplatin | 14.4 ± 1.6 | 0.56 ± 0.08 | 14.7 ± 0.9 |
| 6-BH | >100 | NA | >100 |
| Cisplatin + 2 eq. 6-BH | 11.5 ± 0.7 | 0.87 ± 0.05 | 11.3 ± 2.1 |
| Butyroplatin | 26.1 ± 5.8 | 5.44 ± 0.83 | 33.1 ± 3.9 |
| Platin-B | 1.2 ± 0.2 | 0.057 ± 0.017 | 0.75 ± 0.2 |

Apoptosis Detection by Annexin V Assay

Enhanced activity of Platin-B in A2780/CP70 cells was further confirmed by Annexin-V-propidium iodide (PI) apoptosis-necrosis assay. Specifically, cisplatin resistant A2780/CP70 cells were seeded at a density of 5×10$^5$ cells/mL on each well of a six well plate and allowed to grow overnight. Medium was changed and the cells were treated with 50 µM cisplatin or 50 µM of Platin-B for 12 h at 37° C., As positive controls, etoposide (5 mM, incubation time: 16 h) for apoptosis and $H_2O_2$ (10 mM, incubation time: 1 h) for necrosis were used. The cells were trypsinized, repeatedly washed collecting the supernatants, and centrifuged at 754×g for 3 min, and the supernatants were collected. Cell density was determined and cells were resuspended in 1× annexinV-binding buffer to 1×10$^6$ cells/mL preparing a sufficient volume to have 100 µL per assay. To 100 µL of cell suspension, 5 µL ALEXA FLUOR™ 488 annexin V and 1 µL of 100 µg/mL PI working solution were added, incubated for 15 min at room temperature. After the incubation period, 400 µL of 1× annexin-binding buffer was added to each sample, samples were gently mixed keeping the samples on ice, and the samples were analyzed on the flow cytometer immediately.

Figure 5:
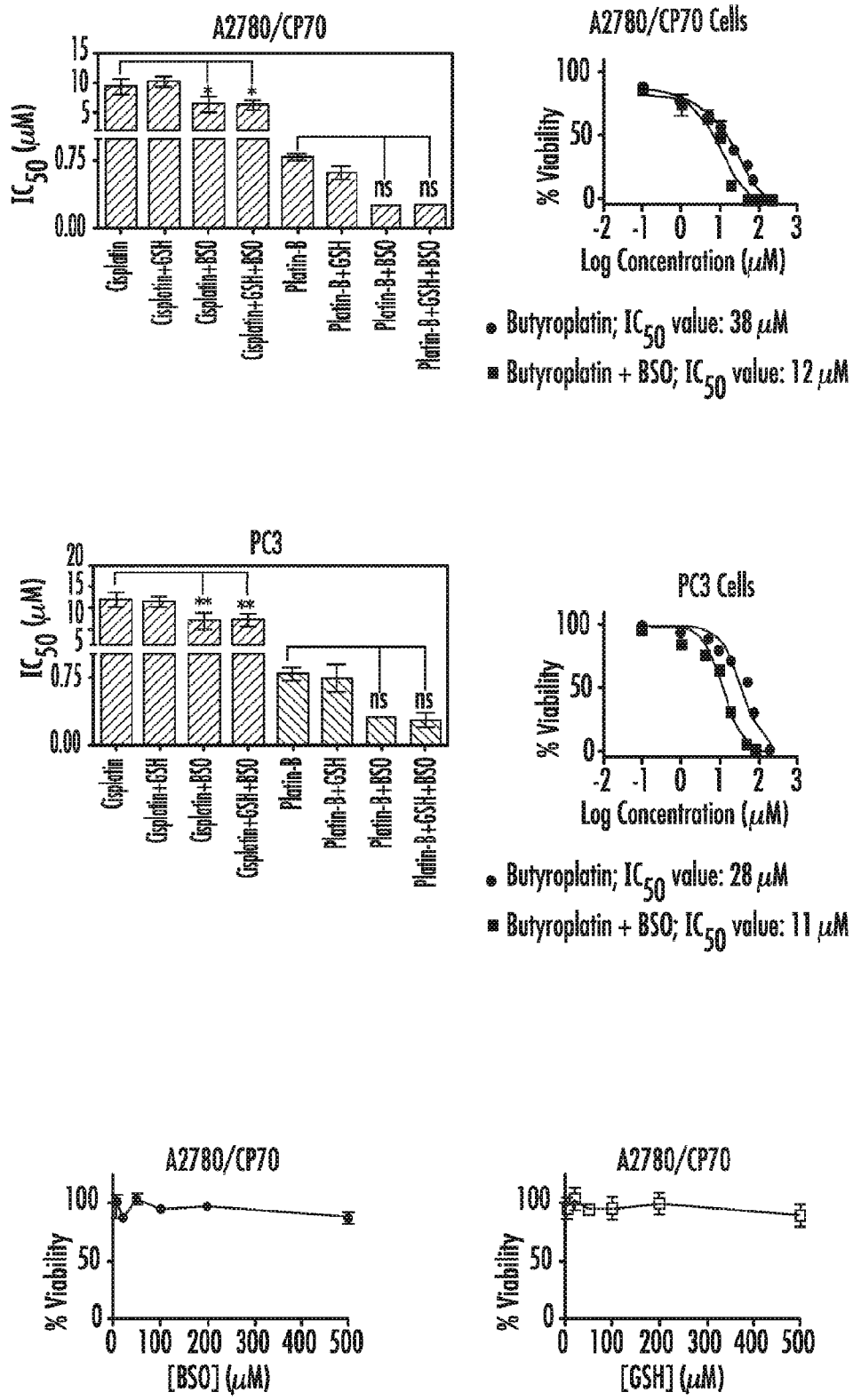
FIG. 5 shows effects of BSO and GSH on cisplatin and Platin-B cytotoxicity on A270/CP70 cells. Cells were incubated either with 0.5 mM BSO for 24 h, with 0.5 mM GSH for 24 h, or with 0.5 mM GSH and 0.5 mM BSO for 24 hr before addition of cisplatin or Platin-B. After incubation with various concentrations of cisplatin or Platin-B for 72 h, cell viability was determined by the MTT method. Values are mean (mean±SD) of three experiments. ns: nonsignificant.

Resistant cells exhibited a high degree of sensitivity to Platin-B compared to cisplatin or other control compounds. GSH homeostasis is important for keeping a well-balanced intracellular redox balance and defense against oxidative stress. The first and rate-limiting step of GSH biosynthesis is catalyzed by γ-GCS, which also modulates the GS-X efflux pump activity. L-buthionine sulfoximine (BSO) is a classical inhibitor of γ-GCS (Hamilton et al., Biochem. Pharmacol., 1985, 34:2583-2586; and Russo, Cancer Res., 1986, 46:2845-2848). BSO decreases the GSH contents however, in many cancer types the GS-x efflux pump activity still remains up regulated. Pretreatment of cancer cells with BSO often abolish the drug resistance caused by the multidrug resistance proteins. Additionally, BSO is known to ameliorate the activity of Pt(IV) prodrugs over Pt(II) in resistant cell lines possibly because of their different metabolic mechanisms (Mistry et al., Int. J. Cancer, 1993, 55:848-856). Cisplatin resistant A2780/CP70 cells were therefore pretreated with BSO and investigated the effects of cisplatin or Platin-B on these pretreated cells (FIG. 5). Pretreatment of A2780/CP70 cells with BSO is expected to deplete GSH levels by inhibiting GSH synthesis. Additionally, in control experiments, cells were also treated with GSH to increase effectively intracellular GSH levels prior to BSO treatment. A diminutive alteration in the cytotoxicity of cisplatin was observed after pretreatment of cells with BSO, GSH, or GSH and (FIG. 5). Conversely, addition of BSO or GSH and BSO, increased the activity of Platin-B in these treated cells (FIG. 5). These results indicate that Platin-B could evade GSH induced deactivation mechanism and work proficiently in the presence of other resistant cell sensitizers such as BSO.

GST Enzymatic Substrate Competitive Assay

GST enzyme modulates GSH to attack on labile electrophilic halide containing molecules in cellular detoxification processes. Cisplatin is believed to get deactivated by GSH through the nucleophilic attack of the GST activated GSH on its labile chlorides. Platin-B, prodrug of cisplatin and 6-BH has two bromide groups that are relatively more labile than chlorides of cisplatin and allow for protection of the prodrug from GSH activity. GST enzymatic activity was evaluated by following the formation of GSH and 1-chloro-2,4-dinitrobenzene (CDNB) adduct. Cisplatin and Platin-B can potentially behave as strong substrate competitor of CDNB and decrease the extent of CDNB-GSH adduct. Hence, GST enzymatic activity was evaluated in presence of cisplatin and Platin-B using enzymatic substrate competitive assay.

This assay was performed according to the instruction given by the manufacturer (GST activity assay kit ab65326). AU the standard solutions were prepared as per the instruction. Samples were prepared in a total 50 µL volume with GST assay buffer, including a negative control with 50 µL of GST assay buffer only and a positive control (10 µL of GST positive control diluted to 1:50) and 40 µL of GST assay buffer only. Sample wells contained 10 µL of GST enzyme diluted to 1:50 and remaining of GST assay buffer. To each well, 5 µL GSH was added. 50 µL of substrate mix containing GST substrate CDNB (5 µL) was prepared. Cisplatin (50 µM or 100 µM) or Platin-B (50 µM or 100 µM) was added to each sample well and incubated for 10 min on an orbital shaker at room temperature. Then, 50 μL of substrate mix was added to each well including controls. The plate was stirred carefully to initiate the reaction and absorbance values were recorded once every minute at 340 nm using a plate reader to obtain 20 data points. GST activity was calculated through the kinetic plot obtained from the time (min) vs. optical density ($OD_{340\ nm}$) using the formula GST activity=$\Delta$A340 min$^{-1}$/0.002777 μM·D/A, where D is the enzyme sample dilution factor and A is the enzyme sample volume added to each well.

Cellular GST Activity Assay

Cellular GST enzymatic activity was also evaluated in lysates isolated from A2780/CP70 cells treated with either cisplatin (50 μM or 100 μM) or Platin-B (50 μM or 100 μM). Briefly, cells were plated in 6 well plate at a density 5×10$^5$ cells per well and allow to grow overnight. These cells were than treated with different concentrations of cisplatin and Platin-B for 24 h. Cells were subsequently scrapped from the tissue culture dish and centrifuged to get pellets. Cell pellets were homogenized in GST assay buffer (1 mL) and centrifuged for 15 min at 10,000×g at 4° C. The resultant supernatants were collected and used for the GST assay as described above.

Figure 6:
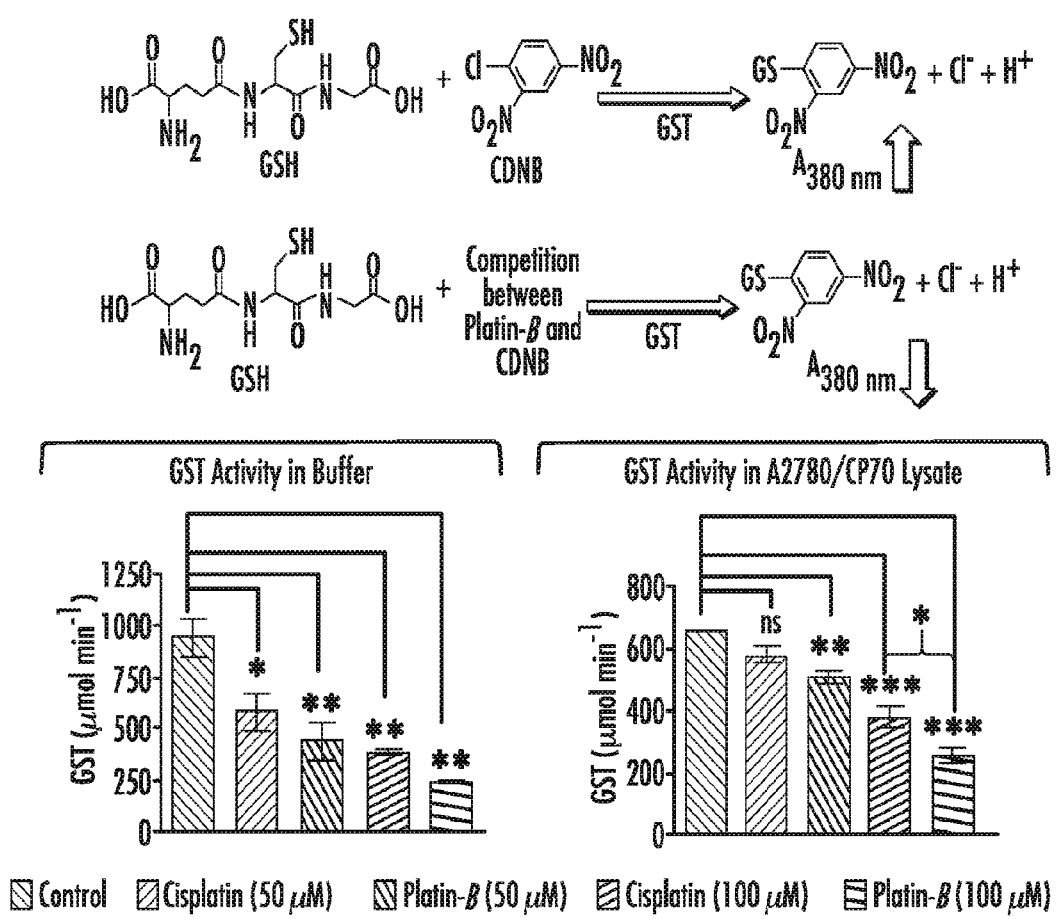
FIG. 6 shows the effect of cisplatin or Platin-B on GST activity in buffer or in A2780/CP70 cells were plated in six well plates ($1 \times 10^6$ cells/well) and incubated at 37° C. overnight. Cisplatin (50 or 100 µM) or Platin-B (50 or 100 µM) were then added to the wells and incubated for 24 h. After incubation, cells were collected by trypsinization, centrifuged, and the supernatants were used for GST activity.

GSH conjugation to Platin-B catalyzed by GST was more efficient than GSH conjugation to cisplatin (FIG. 6). This is due to the presence of two additional Br moieties on Platin-B without deactivating the cisplatin center on the prodrug. Thus the sequential reactions of GSH with cisplatin for detoxification can be avoided when Platin-B is used as a prodrug. Since intracellular GSH is one of the rate-limiting parameters in the detoxification of cisplatin in resistant cell, modulation of intracellular GSH content by using Platin-B as a cisplatin prodrug can be extremely beneficial in the case of resistant cancer with elevated GSH content. Platin-B impaired the GSH contents by its two electrophilic —Br moieties. These results support the clinical approach in depleting GSH for more efficient sensitization of human tumor cells to cisplatin.

Cellular GSH Activity Assay

Figure 7:
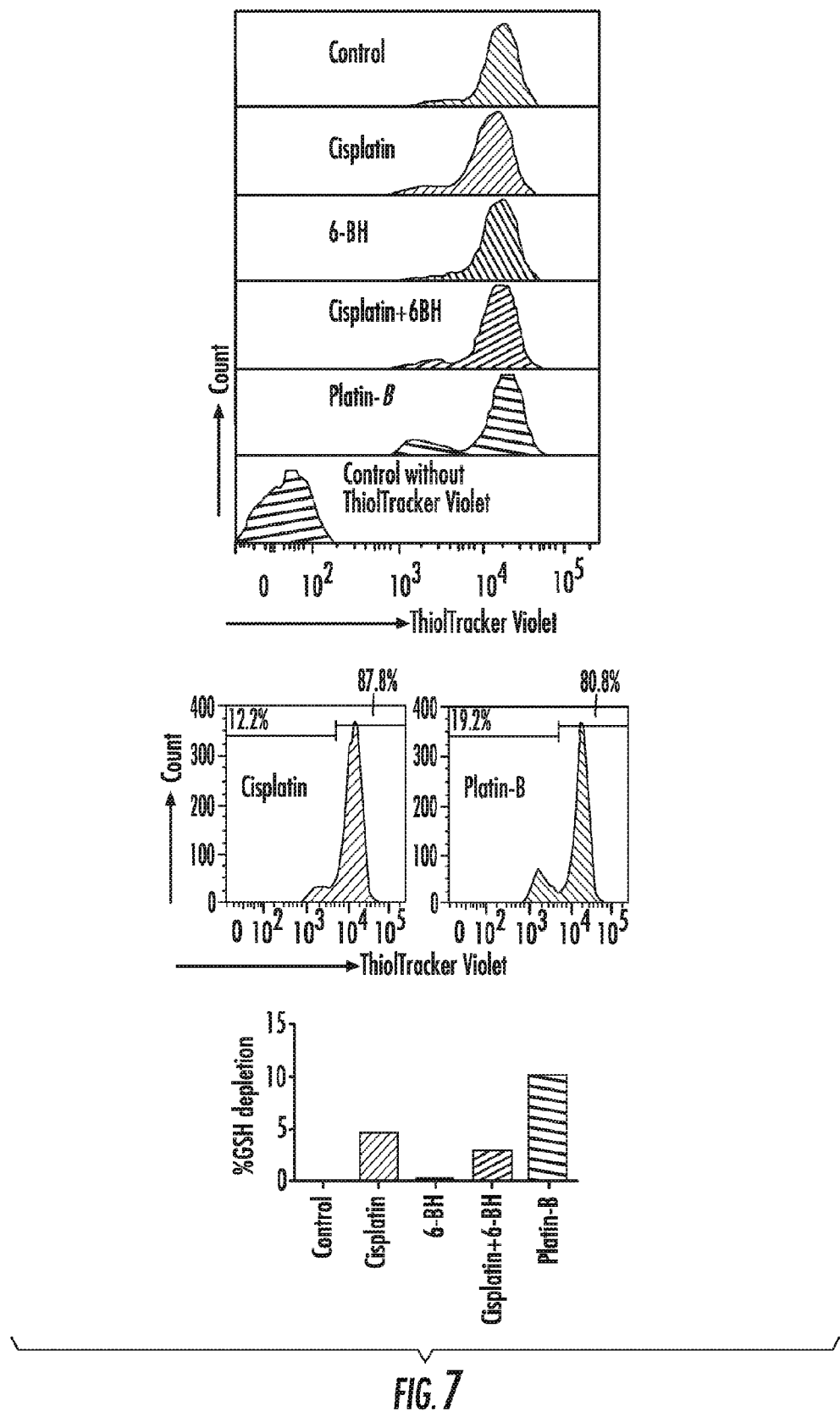
FIG. 7 shows intracellular levels of GSH using flow cytometry in A2780/CP70 cells exposed to cisplatin (10 µM), 6-BH (10 µM), cisplatin (10 µM)+6-BH (20 µM), or Platin-B (10 µM) for 24 h.

The ability of Platin-B to interact with intracellular GSH in A2780/CP70 cells was investigated using the Thiol-Tracker Violet GSH detection reagent. Specifically, A2780/CP70 cells (4×10$^5$ cells/well/2 mL) were plated onto 6 well culture plates and allowed to grow overnight. The medium was removed, and fresh medium was added containing the cisplatin (10 μM) or Platin-B (10 μM), or 6-BH (20 μM), or a mixture of cisplatin (10 μM) and 6-BH (20 μM). After 12 h, both the attached and detached cells were collected by trypsinization, washed with PBS, and resuspended in Dulbecco's PBS (D-PBS) containing $Ca^{2+}$ and $Mg^{2+}$, glucose, and sodium pyruvate. The cells were then incubated with 10 μM (final concentration) ThiolTracker Violet for 30 min at 37° C. The cells were then washed with D-PBS, resuspended in buffer, and immediately analyzed on a flow cytometer with 405 nm excitation and 525 nm emission filters. The ThiolTracker Violet stain is a highly thiol reactive fluorescent probe and can be utilized in effective detection of intracellular GSH by quantitative detection modalities such as flow cytometry. Platin-B (10 μM) demonstrated enhanced ability to reduce GSH levels in these cells in 12 h. Cisplatin at the same concentration had minimal effect on intracellular GSH levels (FIG. 7). Thus, these results further supported the ability of Platin-B to interact with GSH in vitro.

Cellular Uptake Study

Cisplatin resistant A2780/CP70 cells (1×106 cells) were seeded in 6 well plates in 2 mL of RPMI media and incubated for 24 h at 37° C. under 5% $CO_2$ atmosphere. These cells were then treated with Platin-B (10 μM), butyroplatin (10 μM), cisplatin (10 μM), and cisplatin+6-BH (10 μM+20 μM) and subsequently incubated for 12 h at 37° C. with 5% CO2. The media was removed and the cells were washed with PBS (2×1 mL), harvested by trypsinization (0.3 mL), and washed with 0.5 mL media. The solutions containing the cells were centrifuged at 750×g for 3 min at 4° C. and the resultant cell pellet was lysed in Thermo Scientific RIPA cell lysis buffer. The platinum contents in the lysate were measured by ICP-MS and the protein contents were analyzed using Thermo Scientific BCA assay.

Interaction of Platin-B with HK2

Human HK2 (1 μg/mL in PBS) was incubated with Platin-B (1 μM), butyroplatin (1 μM), cisplatin (1 μM), or cisplatin+6-BH (1 and 2 μM, respectively in 1×PBS) at room temperature for 12 h followed by incubation for another 12 h at 4° C. Stock solutions (20 mM) of Platin-B and butyroplatin were made in DMSO and further diluted to 1 μM in 1×PBS. Unreacted platinum compounds were removed by washing the mixtures three times with water using Amicon Ultra Centrifugal Filters (30 kD). HK2 from these samples reconstituted in 1 mL of water and Pt contents were measured by ICP-MS.

Interaction of Platin-B with BSA

BSA (16.5 mg/mL 250 μM) was dissolved in 1×PBS and incubated with 200 μL solution of Platin-B (250 μM), butyroplatin (250 μM), cisplatin (250 μM), or cisplatin+6-BH (250 μM and 500 μM, respectively) at room temperature for 12 h followed by incubation for another 12 h at 4° C. Pt(IV) prodrugs were added in 200 μL of DMSO and this volume of DMSO was also added in all other test articles to maintain the solvent ratio uniform. The unreacted Pt compounds were removed by washing three times with nanopure water using Amicon Ultra Centrifugal Filters (30 kD). BSA samples were reconstituted in 1 mL of water and Pt contents were measured by ICP-MS and protein concentrations were determined by BCA assay.

Citrate Synthase Activity Assay

Figure 8A:
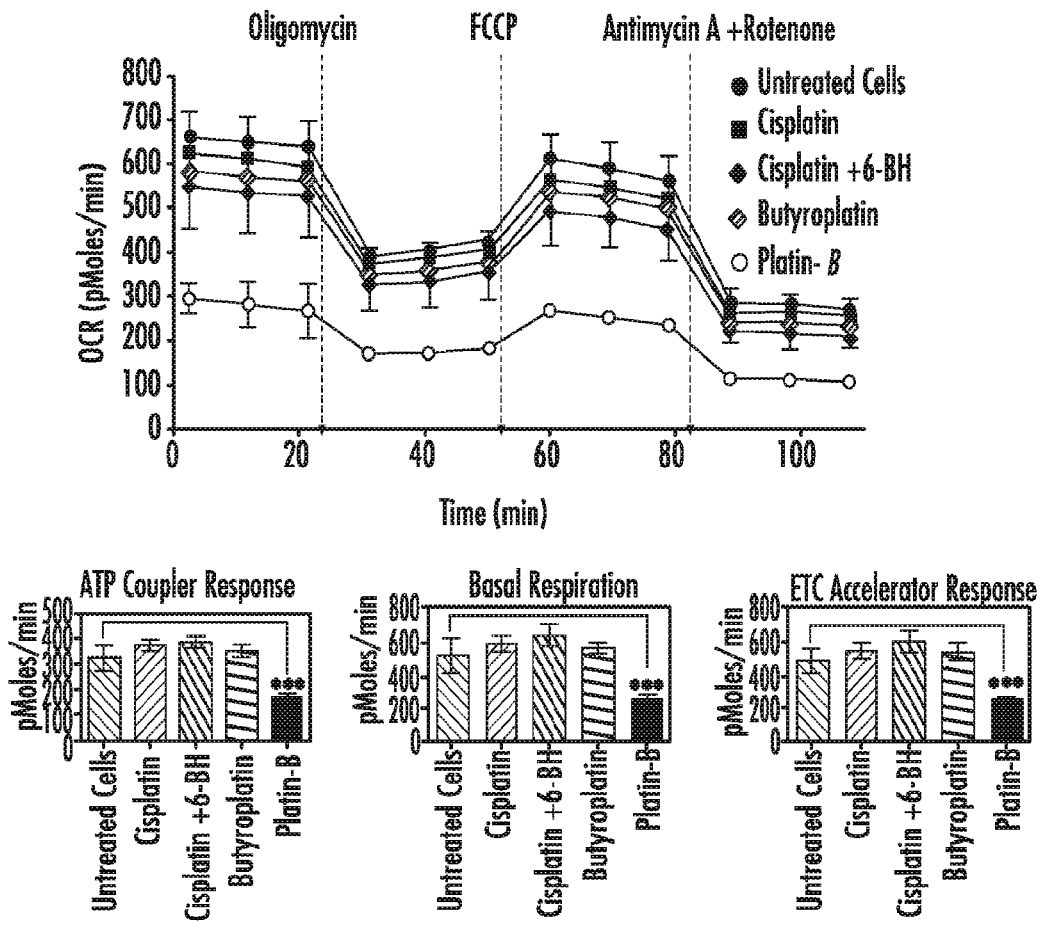
FIG. 8 shows in panel (A) analysis of mitochondrial bioenergetics in A2780/CP70 cells upon treatment with Platin-B (1 µM), cisplatin (1 µM), cisplatin+6-BH (1 µM+2 µM), or butyroplatin (1 µM) for 24 h at 37° C. (B) Citrate synthase activity in A2780/CP70 after treatment with Platin-B (1 µM), cisplatin (1 µM), cisplatin+6-BH (1 µM+2 µM), or butyroplatin (1 µM) for 24 h at 37° C.
Figure 8B:
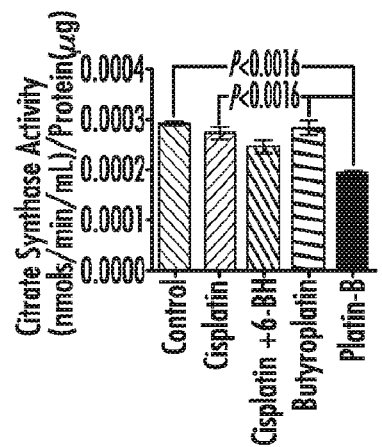

Citrate synthase activity (CS) is a commonly used technique for mitochondrial content; analyses of Platin-B treated A2780/CP70 cells for CS synthase activity suggested a lower mitochondrial content compared to cisplatin, butyroplatin, or a mixture of cisplatin and 6-BH treated cells (FIG. 8, panel B).

Citrate synthase activity assay was performed by following the instruction given in MitoCheck Citrate Synthase Activity assay kit (Cayman item no. 701040). Briefly, A2780/CP70 cells were seeded at a density of 1.2×10$^6$ cells/7 mL in 25 cm$^2$ cell culture flask and grown overnight. Media was aspirated and cells were treated with Platin-B (1 μm), butyroplatin (1 μM), cisplatin (1 μm), or cisplatin+6-BH (1 and 2 μM, respectively) and further incubated for 24 h. The cells were then scraped in presence of fresh media and centrifuged to obtain the cell pellet. The resultant pellet was washed 2 times with 1×PBS and solubilized in 200 μL extraction buffer. This cell suspension was incubated on ice for 20 min followed by centrifugation at 16000×g for 20 minutes at 4° C. The supernatant was collected and used for measuring the citrate synthase activity after 1:200 dilutions. Protein concentration in the samples was measured using BCA assay. As per the protocol, two different solutions of reagents were made to carry out total 60 wells in 96 well plates, such as Tube A which contains 60 μL of each acetyl-CoA reagent and developer reagent in 2880 μL assay buffer, whereas, tube B contains 60 μL of oxaloacetate reagent in 1440 μL of assay buffer. A 50 μL of the contents from tube A were added to each well and then 30 μL of samples were added to their respective well. Finally 20 μL of the substrate oxaloacetate from tube B was added to each well and absorbance was recorded immediately at 412 nm (50 seconds interval for 30 min at room temperature). The citrate synthase activity was calculated through the kinetic plot obtained from the time (min) vs. optical density (OD=412 nm) using the formula: CS Activity=(ΔA412 min−1/5.712 mM−×0.1 mL/0.03 mL)×sample dilution nmoles/min/mL. The citrate synthase activity was further expressed in terms of protein concentrations by dividing nmoles/min/mL by the protein concentration (μg/mL).

Isolation of Platin-B.BSA Adducts for Cellular Uptake and MTT Assay

BSA (16.5 mg/mL, 250 μM) was dissolved in 1×PBS and incubated with 200 μL solution of Platin-B (250 μM) at room temperature for 12 h followed by incubation for another 12 h at 4° C. The unreacted Pt compound was removed by washing with nanopure water three times using Amicon Ultra. Centrifugal Filters (30 kD). Platin-B.BSA sample was reconstituted in 1 mL of water and Pt content was measured by ICP-MS and protein concentration was determined by BCA assay. Cisplatin resistant A2780/CP70 cells ($2×10^6$ cells) were seeded in a 75 $cm^2$ cell culture flask in 15 mL of RPM media and incubated for 24 h at 37° C. under 5% $CO_2$ atmosphere. These cells were then incubated with Platin-B (1 μM) or Platin-B.BSA adduct (1 μM with respect to Platin-B) for 24 h at 37° C. in 5% $CO_2$. The media was removed and the cells were washed with PBS (2×5 mL), harvested by trypsinization (2 mL), and washed with 2 mL of RPMI media. The solutions containing the cells were centrifuged at 750×g for 3 min at 4° C. and the resultant cell pellet was used to fractionate cytosol, nuclei, and mitochondria following the manufactures instruction provided in the Thermo Scientific Mitochondria Isolation Kit (catalog number. 89874). Briefly, cells were homogenized in 800 μL of reagent A and incubated for 2 min in ice following the addition of 10 μL of reagent B and further incubation for 5 min on ice with vortexing every min. After homogenization of the pellet, 800 μL of reagent C was added and the solution was centrifuged at 500×g for 5 min at 4° C. The resultant pellet was used as a nuclei fraction. The supernatant was collected and centrifuged at 14000×g for 30 min at 4° C. The resultant pellet was used as isolated mitochondria and the collected supernatant was used as cytosolic fraction. The platinum contents in each fraction were measured by ICP-MS and the protein contents were analyzed using Thermo Scientific BCA assay. For MTT assay, different concentrations of Platin-B.BSA adduct were added and these concentrations of Platin-B in BSA solution were calculated by ICP-MS.

Platination of Genomic DNA

Cisplatin resistant A2780/CP70 cells ($1×10^6$ cells) were seeded in 6 well plates in 2 mL of RPMI media and incubated for 24 h at 37° C. in 5% $CO_2$ atmosphere. These cells were then treated with Platin-B (1 μM), butyroplatin (1 μM), cisplatin (1 μM), and cisplatin+6-BH (1 μM+2 μM) and subsequently incubated for 24 h at 37° C. The medium was then removed and the cells were washed with PBS (3×0.5 mL), harvested by trypsinization (0.3 mL), and washed with 0.5 mL RPMI media. The solutions containing cells were centrifuged at 750×g for 3 min at 4° C. Genomic DNA was isolated following the Genomic DNA Isolation Kit (ab65358) protocol. Briefly, the cell pellets were lysed in 35 μL of cell lysis buffer via mixing and keeping on ice while vortexing for 5 seconds. The resultant lysate was centrifuged at 18000×g for 3 min at 4° C. The pellet isolated contained the nuclei. The pellet was suspended in 40 μL of cell lysis buffer, followed by addition of 5 μL of enzyme mix. This mixture was homogenized by pipetting several times followed by incubation for 1 h or until the solution becomes clear at 50° C. in water bath. To this solution, 100 μL of absolute ethanol was added; mixed, and the mixture was kept at −20° C. for 10 min. The precipitated DNA was isolated by centrifuging at 18000×g for 5 min at room temperature. The supernatant was removed to get the isolated genomic DNA as a pellet. The pellet was washed 2 times with 1 mL of 70% ethanol and centrifuged at 18000×g for 5 min at room temperature. The resultant genomic DNA was re-suspended in 20 μL of Tris-EDTA (TE) buffer followed by determination of DNA concentrations by Nanodrop instrument. Platinum contents in the samples were analyzed using ICP-MS.

Platination of Mitochondrial DNA

Cisplatin resistant A2780/CP70 cells ($5×10^6$ cells) were seeded in 150 $cm^2$ cell culture flask in 25 mL of RPMI: media and incubated for 24 h at 37° C. with 5% $CO_2$. These cells were then treated with Platin-B (1 μM), butyroplatin (1 μM), cisplatin (1 μM), or cisplatin+6-BH (1 μM+2 μM) and subsequently incubated for 24 h at 37° C. The medium was then removed and the cells were washed with ice cold PBS (3×5 mL), harvested by trypsinization (5 mL), and washed with 5 mL RPMI media. The solutions containing the cells were centrifuged at 750×g for 3 min at 4° C. to get a cell pellet. Mitochondrial DNA was isolated following the mitochondrial DNA Isolation Kit (ab65321) protocol. The cell pellets were re-suspended in 1 mL of 1× cytosol extraction buffer followed by incubation for 10 min on ice. The cells were then homogenized in ice-cold Dounce tissue grinder (1 mL capacity) using 50-60 strokes. The efficiency of homogenization was checked by observing the disappearance of shiny ring around the nucleus by pipetting 2-3 μL of homogenized cell suspension on to cover slip followed by the observation under microscope. The resultant homogenized cell suspension was centrifuged at 700×g for 10 min at 4° C. to remove nuclei and intact cells. The supernatant was transferred to a new 1.5 mL tube and centrifuged at 1.0000×g for 30 min at 4° C. The resultant pellet was resuspended in 1 mL of cytosol extraction buffer and centrifuged again at 10000×g for 30 min at 4° C. The resultant pellet was isolated as mitochondrial fraction. The mitochondrial fraction was lysed in 30 μL of mitochondria lysis buffer and kept on ice for 10 min. To this, 5 μL of enzyme mix was added and mixed thoroughly, followed by incubation for 1 h or until the solution becomes clear at 50° C. in water bath. To this solution, 100 μL of absolute ethanol was added, mixed thoroughly, and kept at −20° C. for 10 min. The precipitated DNA was isolated by centrifuging at 18000×g for 5 min at room temperature. The supernatant was removed to get the isolated mitochondrial DNA as a pellet. The pellet was washed with 1 mL of 70% ethanol 4 times and centrifuged at 18000×g for 5 min at room temperature. The resultant mitochondrial DNA was re-suspended in 2.0 μL of TE buffer followed by determination of DNA concentrations using Thermo-scientific Nanodrop instrument. Platinum contents in the samples were analyzed using ICP-MS.

MitoStress Test Analysis

To understand the cellular metabolism and mitochondrial profile upon treatment with different compounds, four parameters of mitochondrial functions, rate of basal respiration, ATP linked respiration, proton leak, and spare respiratory capacity were investigated by using Seahorse XF-24 cell Mito Stress Test Kit. Prior to the assay, XF sensor cartridges were hydrated. To each well of XF utility plate, 1.5 mL of Seahorse Bioscience XF calibrant (pH=7.4) was added and the XF sensor cartridges were placed on top of the utility plate at 37° C. without $CO_2$ for a minimum of 12 h. PC3 and A2780/CP70 cells were cultured in XF24-well cell culture microplates (Seahorse Bioscience) at a density of 40×103 cells/well in 200 μL growth medium and then incubated for 24 h at 37° C. in 5% $CO_2$ atmosphere. The cells were treated with Platin-B (1 μM), cisplatin (1 μM), cisplatin+6-BH (1 μM+2 μM) and butyroplatin (1 μM) for 24 h at 37° C. in 5% $CO_2$ atmosphere. After 24 h, 150 μL of the culture medium was removed from each well and the cells were rinsed three times with 450 μL of XF DMEM assay media pre-warmed to 37° C. and finally 450 μL of XF DMEM assay media was added to each well and the plate was placed at 37° C. without $CO_2$ for 1 h prior to assay. Different parameters of respiration were calculated by subtracting the average OCR before and after the addition of the electron transport inhibitors oligomycin (1.0 μM), FCCP (1.0 μM), an ionophore that is a mobile ion carrier, and a mixture of antimycin-A (1.0 μM) which is a complex III inhibitor and rotenone (1.0 μM), a mitochondrial inhibitor that prevents the transfer of electrons from the Fe—S center in Complex I to ubiquinone. The parameters calculated included: basal respiration (baseline respiration minus antimycin-A post injection respiration), ATP turnover (baseline respiration minus oligomycin post injection respiration), maximal respiratory capacity (FCCP stimulated respiration minus antimycin-A post injection respiration) and reserve respiratory capacity (FCCP stimulated respiration minus baseline respiration). Test articles on each well had four replicates.

Figure 9:
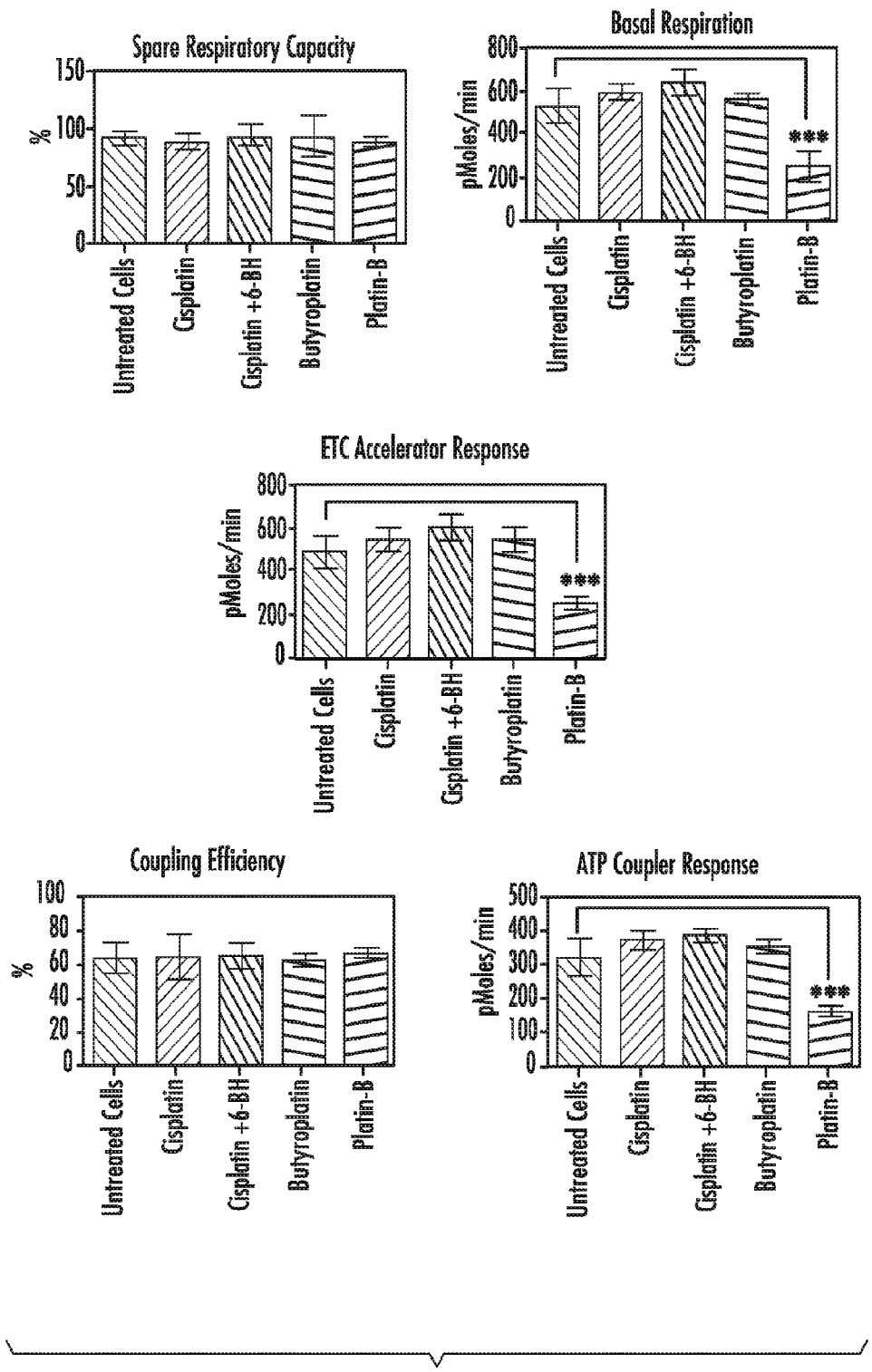
FIG. 9 shows a comparison of different parameters related to mitochondrial respiration in A2780/CP70 cells treated with Platin-B (1 µM), cisplatin (1 µM), cisplatin+6-BH (1 µM+2 µM), or butyroplatin (1 µM) for 24 h at 37° C. in 5% $CO_2$ atmosphere.
Figure 10A:
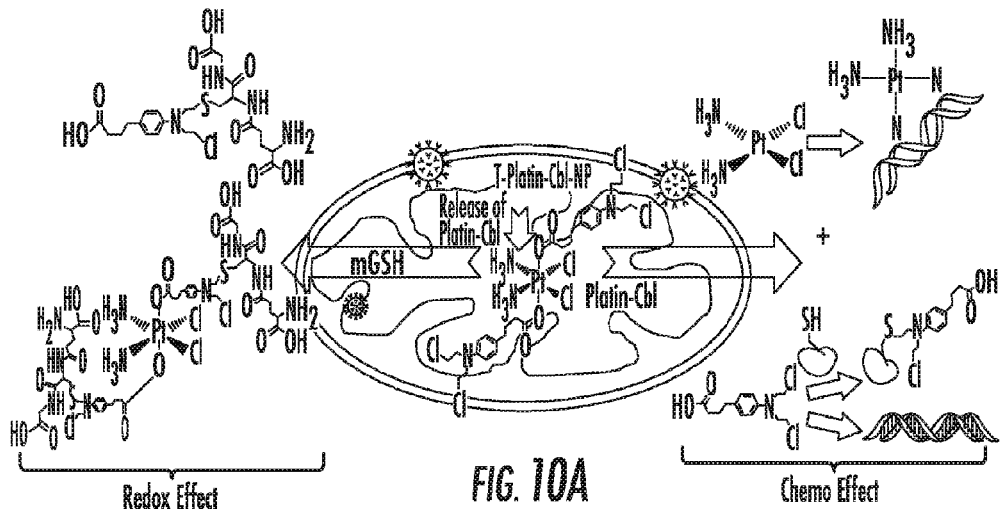
FIG. 10, Panel (A), shows hypothesized mechanism of action of Platin-Cbl. Panel (B) shows the synthesis of Platin-Cbl.
Figure 10B:
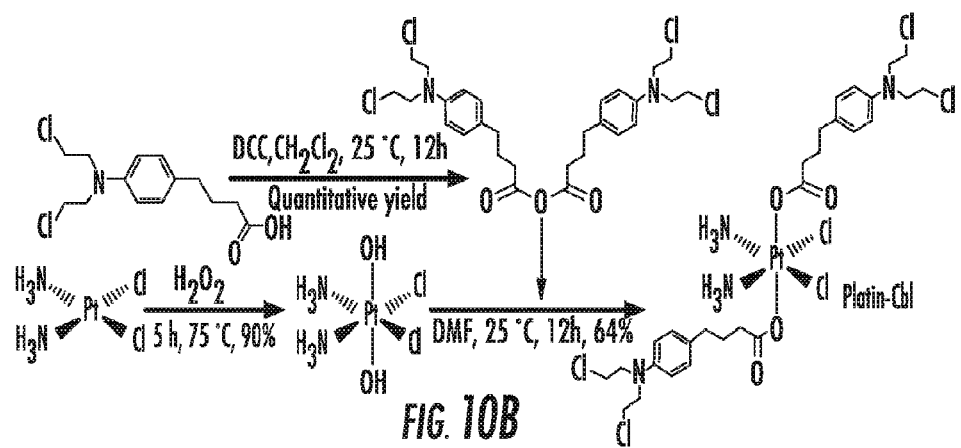
Figure 13:
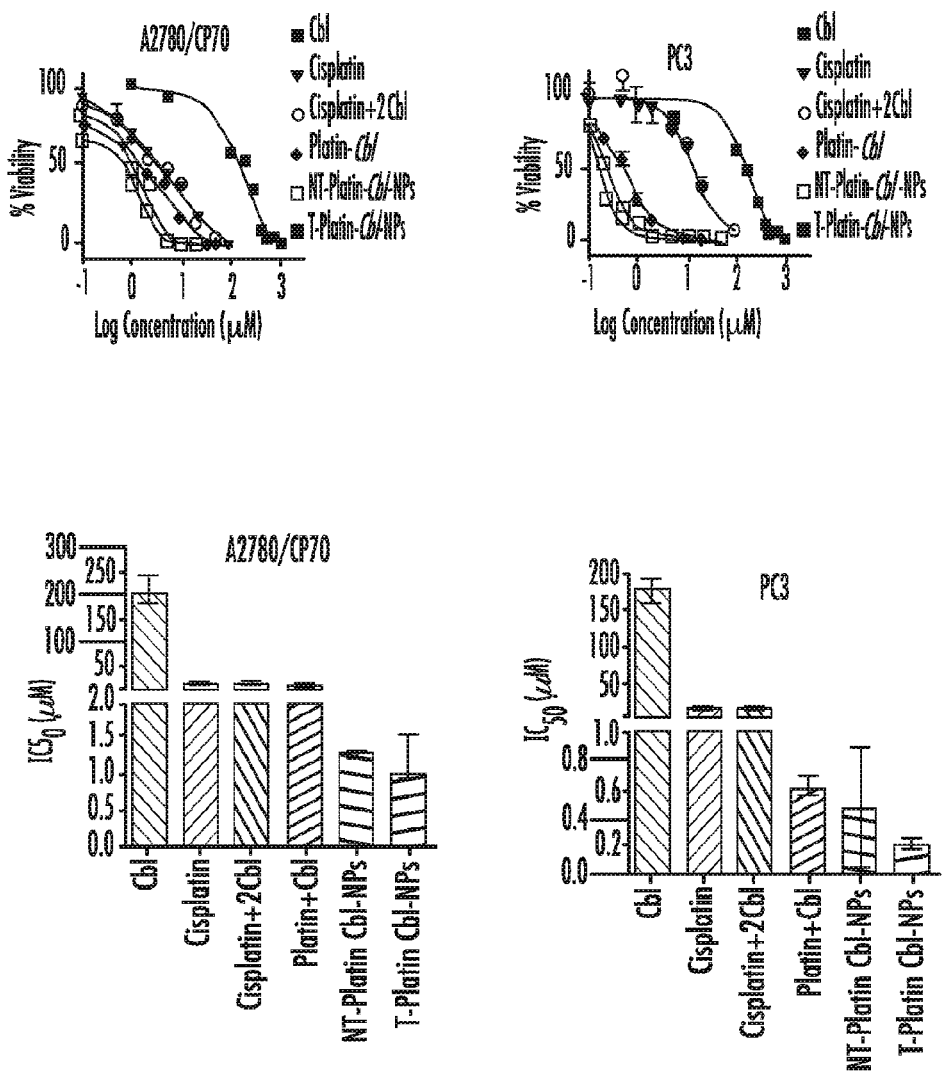
FIG. 13 shows the $IC_{50}$ values of chlorambucil (Cbl), cisplatin, cisplatin+2Cbl, Platin-Cbl, NT-Platin-Cbl-NP, T-Platin-Cbl-NP in prostate cancer PC3 and cisplatin resistant ovarian cancer A2780/CP70 cells as determined by the MTT assay.
Figure 14:
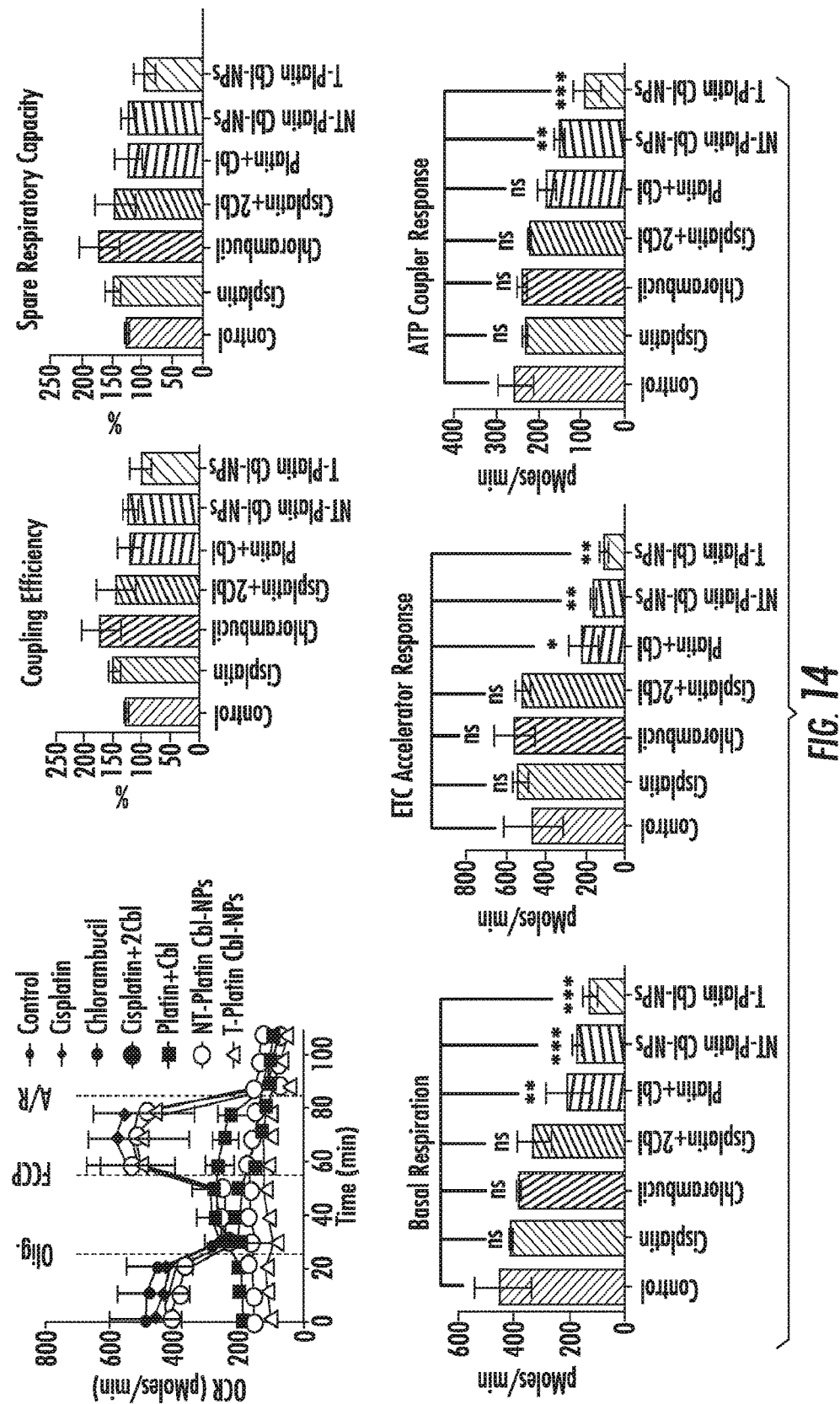
FIG. 14 is a groups of graphs showing the analysis of mitochondrial bioenergetics in A2780/CP70 cells upon treatment with chlorambucil (Cbl), cisplatin, cisplatin+2Cbl, Platin-Cbl, NT-Platin-Cbl-NP, T-Platin-Cbl-NP in prostate cancer PC3 and cisplatin resistant ovarian cancer A2780/CP70 cells using Seahorse analyzer. Coupling Efficiency=1-ATP Coupler Response/Basal Respiration; Spare Respiratory Capacity=ETC Accelerator Response/Basal Respiration; Basal Respiration=The 3rd Basal Measurement; ETC Accelerator Response=The maximum rate after FCCP injection; ATP Coupler Response=The minimum rate after ATP coupler injection.

Analyses of the OCR values vs. time and parameters associated with mitochondrial respiration indicated that Platin-B inhibited mitochondrial respiration significantly. Cisplatin, butyroplatin, or a mixture of cisplatin and 6-BH did not demonstrate such activities on mitochondrial respiration of these cells (FIG. 8, panel A, and FIG. 9). Thus, the OCR levels and decreased CS activity in Platin-B treated cisplatin resistant cells further strengthen the claim that the mitochondrion is one of the targets for this Pt(IV) prodrug.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A compound of Formula I:

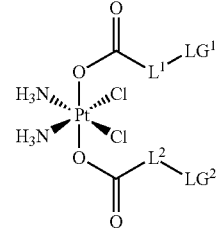

wherein $L^1$ and $L^2$ are each —$(CH_2)_n$—, where n is 5-15, and $LG^1$ and $LG^2$ are each Cl, Br, or I.

2. The compound of claim 1, wherein n is 5-10.

3. The compound of claim 1, wherein the compound has Formula IA-1:

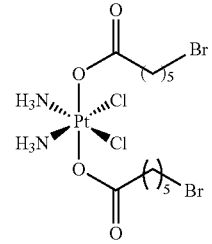

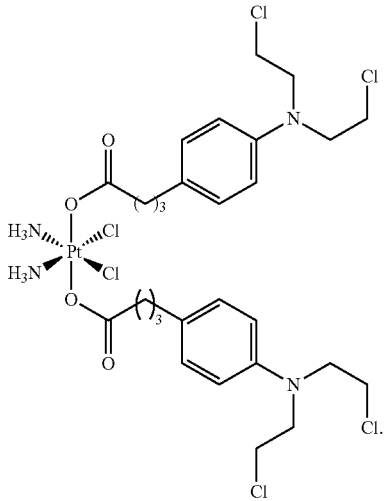

4. A pharmaceutical composition, comprising a compound of claim 1 and a pharmaceutically acceptable carrier.

5. The composition of claim 4, wherein the composition is a liposomal formulation, emulsion, or dispersion.

6. A pharmaceutical composition, comprising a compound of claim 1 and a nanoparticle or microcapsule.

7. A nanoparticle comprising a compound of claim 1.

* * * * *

UNITED STATES PATENT AND TRADEMARK OFFICE
CERTIFICATE OF CORRECTION

PATENT NO. : 10,457,700 B2  
APPLICATION NO. : 15/555693  
DATED : October 29, 2019  
INVENTOR(S) : Shanta Dhar and Rakesh Pathak Page 1 of 1

It is certified that error appears in the above-identified patent and that said Letters Patent is hereby corrected as shown below:

In the Claims

Column 40, Claim 3, Lines 33-53, delete the formula:

"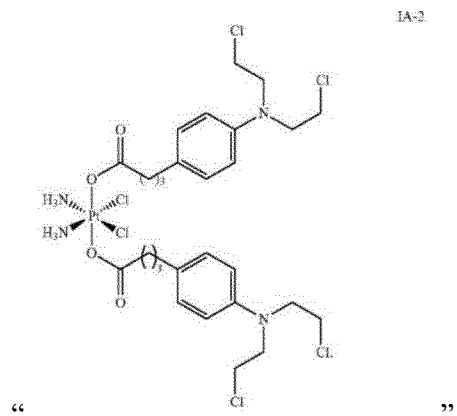"

Signed and Sealed this  
Second Day of June, 2020

Andrei Iancu  
*Director of the United States Patent and Trademark Office*